United States Patent
Scheiner

(10) Patent No.: US 10,195,428 B2
(45) Date of Patent: Feb. 5, 2019

(54) NEURAL STIMULATION TO TREAT SLEEP APNEA

(71) Applicant: Medtronic, Inc., Minneapolis, MN (US)

(72) Inventor: Avram Scheiner, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/279,383

(22) Filed: Sep. 28, 2016

(65) Prior Publication Data

US 2017/0087360 A1     Mar. 30, 2017

Related U.S. Application Data

(60) Provisional application No. 62/234,434, filed on Sep. 29, 2015.

(51) Int. Cl.
| | |
|---|---|
| *A61N 1/00* | (2006.01) |
| *A61N 1/36* | (2006.01) |
| *A61F 5/56* | (2006.01) |
| *A61B 5/11* | (2006.01) |
| *A61B 5/00* | (2006.01) |

(Continued)

(52) U.S. Cl.
CPC .......... *A61N 1/3601* (2013.01); *A61B 5/1116* (2013.01); *A61B 5/4809* (2013.01); *A61F 5/566* (2013.01); *A61N 1/0548* (2013.01); *A61N 1/3611* (2013.01); *A61N 1/36135* (2013.01); *A61N 1/36139* (2013.01); *A61N 1/36167* (2013.01); *A61N 1/37229* (2013.01)

(58) Field of Classification Search
CPC ..... A61B 5/1116; A61B 5/4809; A61F 5/566; A61N 1/0548; A61N 1/3601; A61N 1/3611; A61N 1/36135; A61N 1/36139; A61N 1/36167; A61N 1/37229
See application file for complete search history.

(56) References Cited

U.S. PATENT DOCUMENTS

| | | |
|---|---|---|
| 2,999,232 A | 9/1961 | Wilson |
| 3,032,029 A | 5/1962 | Cunningham |
| 3,480,010 A | 11/1969 | Crossley |

(Continued)

FOREIGN PATENT DOCUMENTS

WO    WO 2010/090852 A2    8/2010

OTHER PUBLICATIONS

Sanders et al., "Three-Dimensional Atlas of Human Tongue Muscles", The Anatomical Record 296:1102-1114 (2013), 14 pages.

(Continued)

*Primary Examiner* — George Manuel

(57) ABSTRACT

A removable oral device is disclosed. The removable oral device comprises a mounting retainer configured to align with a set of teeth. An electrical stimulator is coupled to the mounting retainer. A single lead is employed that has a first and a second end and lacking a mechanical connection to the mounting retainer. A first and a second electrode are positioned along the single lead. The lead is disposed perpendicular to a longitudinal axis of a patient's tongue such that the first electrode is proximate a first hypoglossal nerve and the second electrode is proximate a second hypoglossal nerve.

37 Claims, 26 Drawing Sheets

(51) Int. Cl.
*A61N 1/05* (2006.01)
*A61N 1/372* (2006.01)

(56) References Cited

U.S. PATENT DOCUMENTS

| | | | |
|---|---|---|---|
| 3,593,703 A | 7/1971 | Gunn | |
| 3,696,377 A | 10/1972 | Wall | |
| 3,998,209 A | 12/1976 | Macvaugh | |
| 4,220,142 A | 9/1980 | Rosen et al. | |
| 4,304,227 A | 12/1981 | Samelson | |
| 4,593,686 A | 6/1986 | Lloyd et al. | |
| 4,830,008 A | 5/1989 | Meer | |
| 6,212,435 B1 | 4/2001 | Lattner et al. | |
| 6,618,627 B2 | 9/2003 | Lattner et al. | |
| 7,711,438 B2 | 5/2010 | Lattner et al. | |
| 8,574,164 B2 | 11/2013 | Mashiach | |
| 8,577,464 B2 | 11/2013 | Mashiach | |
| 8,577,465 B2 | 11/2013 | Mashiach | |
| 8,577,466 B2 | 11/2013 | Mashiach | |
| 8,577,467 B2 | 11/2013 | Mashiach | |
| 8,577,468 B2 | 11/2013 | Mashiach | |
| 8,577,472 B2 | 11/2013 | Mashiach | |
| 8,577,478 B2 | 11/2013 | Mashiach | |
| 8,585,617 B2 | 11/2013 | Mashiach | |
| 8,588,941 B2 | 11/2013 | Mashiach | |
| 8,644,947 B2 | 2/2014 | Mashiach | |
| 8,700,183 B2 | 4/2014 | Mashiach | |
| 8,718,776 B2 | 5/2014 | Mashiach | |
| 8,751,005 B2 | 6/2014 | Meadows et al. | |
| 8,812,113 B2 | 8/2014 | Mashiach | |
| 8,812,135 B2 | 8/2014 | Mashiach | |
| 8,831,730 B2 | 9/2014 | Mashiach | |
| 8,838,256 B2 | 9/2014 | Mashiach | |
| 8,886,322 B2 | 11/2014 | Meadows et al. | |
| 8,897,880 B2 | 11/2014 | Mashiach | |
| 8,903,515 B2 | 12/2014 | Mashiach | |
| 8,909,341 B2 | 12/2014 | Gelfand et al. | |
| 8,948,871 B2 | 2/2015 | Mashiach | |
| 8,958,893 B2 | 2/2015 | Mashiach | |
| 9,031,653 B2 | 5/2015 | Mashiach | |
| 9,061,162 B2 | 6/2015 | Mashiach | |
| 9,077,022 B2 | 7/2015 | Howard et al. | |
| 9,095,725 B2 | 8/2015 | Mashiach | |
| 9,155,899 B2 | 10/2015 | Mashiach | |
| 9,403,009 B2 | 8/2016 | Mashiach | |
| 9,409,013 B2 | 8/2016 | Mashiach | |
| 9,415,215 B2 | 8/2016 | Mashiach | |
| 9,415,216 B2 | 8/2016 | Mashiach | |
| 2002/0049479 A1 | 4/2002 | Pitts | |
| 2003/0069626 A1 | 4/2003 | Lattner et al. | |
| 2009/0078274 A1 | 3/2009 | Bhat et al. | |
| 2010/0010385 A1 | 1/2010 | Skelton et al. | |
| 2010/0204614 A1* | 8/2010 | Lindquist | A61B 5/11 600/586 |
| 2011/0093036 A1 | 4/2011 | Mashiach | |
| 2011/0152965 A1 | 6/2011 | Mashiach | |
| 2013/0042876 A1* | 2/2013 | Hermanson | A61F 5/566 128/848 |
| 2013/0072747 A1 | 3/2013 | Mashiach | |
| 2013/0072999 A1 | 3/2013 | Mashiach | |
| 2013/0079843 A1 | 3/2013 | Mashiach | |
| 2013/0085537 A1 | 4/2013 | Mashiach | |
| 2013/0085540 A1 | 4/2013 | Mashiach | |
| 2013/0085541 A1 | 4/2013 | Mashiach | |
| 2013/0085542 A1 | 4/2013 | Mashiach | |
| 2013/0085543 A1 | 4/2013 | Mashiach | |
| 2013/0085544 A1 | 4/2013 | Mashiach | |
| 2013/0085545 A1 | 4/2013 | Mashiach | |
| 2013/0085558 A1 | 4/2013 | Mashiach | |
| 2013/0085559 A1 | 4/2013 | Mashiach | |
| 2013/0085560 A1 | 4/2013 | Mashiach | |
| 2013/0085561 A1 | 4/2013 | Mashiach | |
| 2014/0031840 A1 | 1/2014 | Mashiach | |
| 2014/0031889 A1 | 1/2014 | Mashiach | |
| 2014/0031890 A1 | 1/2014 | Mashiach | |
| 2014/0031891 A1 | 1/2014 | Mashiach | |
| 2014/0031892 A1 | 1/2014 | Mashiach | |
| 2014/0031913 A1 | 1/2014 | Mashiach | |
| 2014/0031914 A1 | 1/2014 | Mashiach | |
| 2014/0031915 A1 | 1/2014 | Mashiach | |
| 2014/0031916 A1 | 1/2014 | Mashiach | |
| 2014/0039579 A1 | 2/2014 | Mashiach | |
| 2014/0052212 A1 | 2/2014 | Mashiach | |
| 2014/0107727 A1 | 4/2014 | Mashiach | |
| 2014/0135868 A1 | 5/2014 | Bashyam | |
| 2014/0323839 A1 | 10/2014 | McCreery | |
| 2014/0371822 A1 | 12/2014 | Mashiach | |
| 2014/0371823 A1 | 12/2014 | Mashiach | |
| 2014/0371824 A1 | 12/2014 | Mashiach | |
| 2015/0190630 A1 | 7/2015 | Kent et al. | |
| 2016/0030739 A1 | 2/2016 | Mashiach | |
| 2016/0030740 A1 | 2/2016 | Mashiach | |

OTHER PUBLICATIONS

Physician Programmer Model 8840, User Manual, Jul. 2010, 14 pages.
Medtronic's Patient Programmer Model 37642, Apr. 2015, 152 pages.
Physician Programmer Model 8840, Technical Manual, 2016, 72 pages.
(PCT/US2016/054451) PCT Notification of Transmittal of the International Search Report and the Written Opinion of the International Searching Authority, dated Dec. 16, 2016, 12 pages.

* cited by examiner

NEURAL STIMULATION TO TREAT SLEEP APNEA

This application claims the benefit of U.S. Provisional Application Ser. No. 62/234,434 by Scheiner, which was filed on Sep. 29, 2015, and is titled "HYPOGLOSSAL NERVE STIMULATION FOR SLEEP APNEA THERAPY THROUGH ORAL ACCESS." U.S. Provisional Application Ser. No. 62/234,434 by Scheiner is incorporated herein by reference in its entirety.

TECHNICAL FIELD

The present disclosure relates generally to devices and methods for treating sleep apnea; and, more particularly, to a neural stimulator configured to deliver electrical stimulation to neural tissue through a medical electrical lead that is not mechanically connected to the neural stimulator.

BACKGROUND

Moderate to severe obstructive sleep apnea (OSA), which encompasses apnea and hypopnea, is a serious disorder that affects millions of people on a daily basis such that their breathing is repeatedly stopped and started on an irregular basis thereby reducing oxygen levels in their blood stream. OSA is caused by complete or partial collapse of the pharynx during sleep. In particular, muscles in a patient's throat intermittently relaxes thereby blocking the upper airway while sleeping. Airflow into the upper airway can be blocked by the tongue moving to the back of the throat and covering a smaller than normal airway. Loss of airflow causes low oxygen saturation levels in the blood. Lack of adequate levels of oxygen can contribute to abnormal heart rhythms, heart attack, heart failure, high blood pressure, stroke, memory problems and increased accidents. Loss of air flow also causes unusual inter-thoracic pressure as a person tries to breathe with a blocked airway. Additionally, loss of sleep occurs when a person is awakened during an apneic episode.

Conventional treatment methods have been employed with varying degrees of success. For example, hypoglossal nerve stimulation (HGNS) has been used to move the tongue forward in the mouth to clear the airway. Some conventional HGNS therapy systems require the use of a cuff electrode wrapped around the hypoglossal nerve (HGN) to deliver therapy, as shown in U.S. Pat. No. 8,751,005 to Meadows et al. Implanting a cuff electrode is an invasive procedure requiring neuro-surgical skills. Additionally, there are occasions when nerve damage can occur due to attaching the cuff electrode to the nerve. Numerous other methods are disclosed for pacing neural tissue to address OSA such as U.S. Pat. No. 8,751,005 to Paul Meadows et al., US Pregrant Application No. US20020049479 to Pitts. US20140135868 to Bashyam, U.S. Pat. No. 8,909,341 to Gelfand et al., Inc., WO2010090852 to Lindquist et al., US Patent Application No. 20140323839 to Huntington et al. While conventional treatments have alleviated some of the OSA symptoms, disadvantages still exist with conventional devices and methods. It is therefore desirable to develop additional methods and systems that overcome the disadvantages associated with conventional OSA treatments.

SUMMARY

The present disclosure relates to a neural stimulation device for treating obstructive sleep apnea (OSA). The neural stimulation device comprises a mounting retainer configured to align with a set of teeth, an electrical stimulator and transmitting antenna coupled to the mounting retainer, and a single lead having a first and a second end that lacks a mechanical connection to the mounting retainer. The lead includes a first and a second electrode positioned along the single lead. The lead is placed in the base of the tongue near a first and/or second hypoglossal nerve. The lead is disposed perpendicular to a longitudinal axis of a patient's tongue such that the first electrode is near a first hypoglossal nerve and the second electrode is near a second hypoglossal nerve. In one or more embodiments, the device does not need to synchronize stimulation with breathing. In one or more embodiments, the device lacks a sensor to sense respiration.

One or more embodiments are directed to a method for treating OSA. The method comprises that with a processor, controlling a stimulation generator to alternately and wirelessly deliver electrical stimulation to first and second tissue sites proximate to first and second hypoglossal nerves, respectively, of a patient to cause at least a portion of a tongue to move.

Numerous benefits are achieved by the neural stimulation device described herein. First, neuro-surgical skills are not required for inserting the lead into the base of the tongue and snapping a retainer, with an electrical stimulator, over the lower set of teeth. Second, the technique can be performed in a short period of time without much equipment or medical support. Third, less risk and morbidity is experienced compared to conventional devices. For example, pacing electrodes of the present disclosure do not need to contact the nerve as is required by a cuff electrode employed by conventional devices. Fourth, a scar is not visible due to the technique merely implanting a lead into the base of the tongue. Fifth, the lead could be easily removed, if necessary. To remove the lead, a small incision on one side of the tongue is made to expose the lead. The lead would then be pulled out from that side.

Sixth, efficacy of bilateral stimulation of the hypoglossal nerves is improved by very close placement of a single lead near both hypoglossal nerves compared to most conventional devices that use an oral device yet did not disclose placement of the electrode sufficiently near two nerves. Seventh, the neural stimulation device, according to one or more embodiments, lacks a sensor(s) since no monitoring of breathing (e.g. inspiration and/or exhalation) is required because both hypoglossal nerves undergo stimulation while the patient sleeps and then automatically shuts off by, for example, a timer connected to the processor. Additionally, the stimulation can be dithered between the two nerves to avoid fatigue by the hypoglossal nerves to the signal. In one embodiment, one hypoglossal nerve is electrically stimulated while stimulation is off for the other hypoglossal nerve. For example, the stimulation is not delivered to the first nerve while stimulation is electrically delivered to the second nerve.

Eighth, the open loop stimulation system can be switched between the electrical stimulation field of one or both hypoglossal nerves to avoid fatigue of the nerves. Ninth, an implantable stimulator is not needed since the neural stimulator is mounted on a removable mouth piece. Tenth, a rechargeable or replaceable battery is attached to the mouth piece allowing for easy replacement of the battery. Eleventh, the lead is not directly mechanically connected to the pulse generator but is instead wirelessly connected to the pulse generator through energy transfer. For example, the energy is transferred by induction via an inductive coupling.

DETAILED DESCRIPTION

Figure 1:
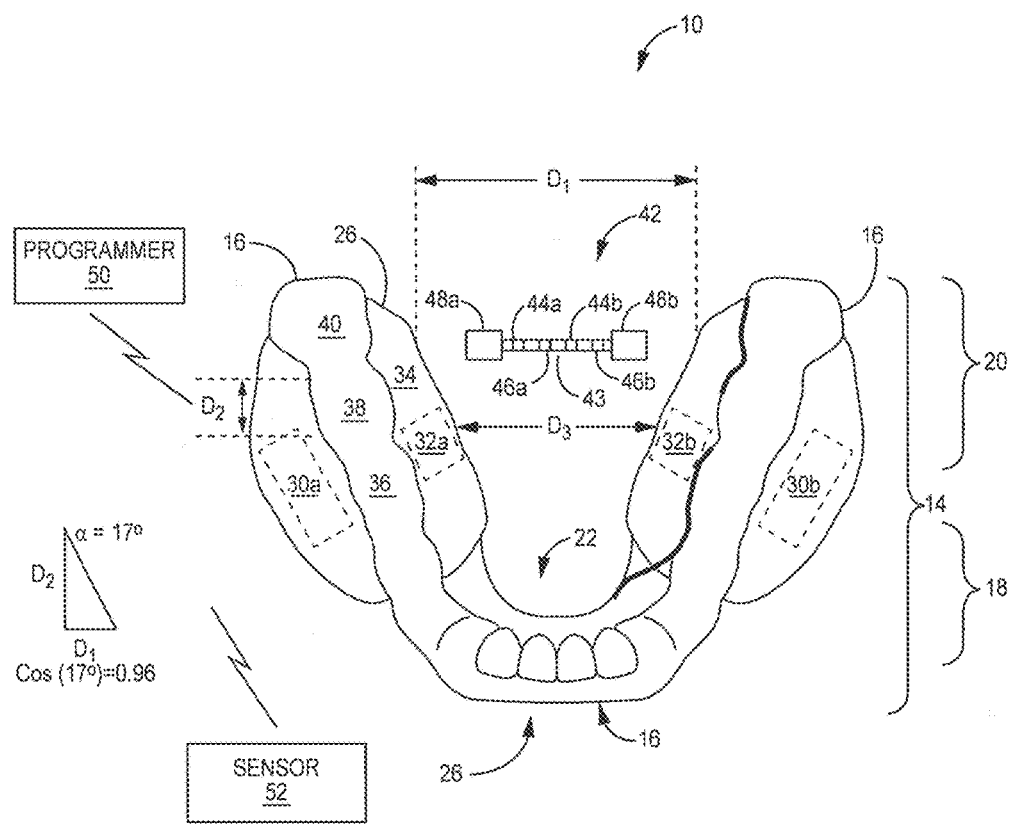
FIG. 1 is a conceptual diagram illustrating a dental system comprising a removable oral device, placed over a set of teeth, in electrical communication with a lead positioned in the musculature of a tongue to cause a portion of the tongue to move.

The following description of the preferred embodiments is merely exemplary in nature and is in no way intended to limit the invention, its application, or uses. For purposes of clarity, similar reference numbers are used in the drawings to identify similar elements.

Figure 2:
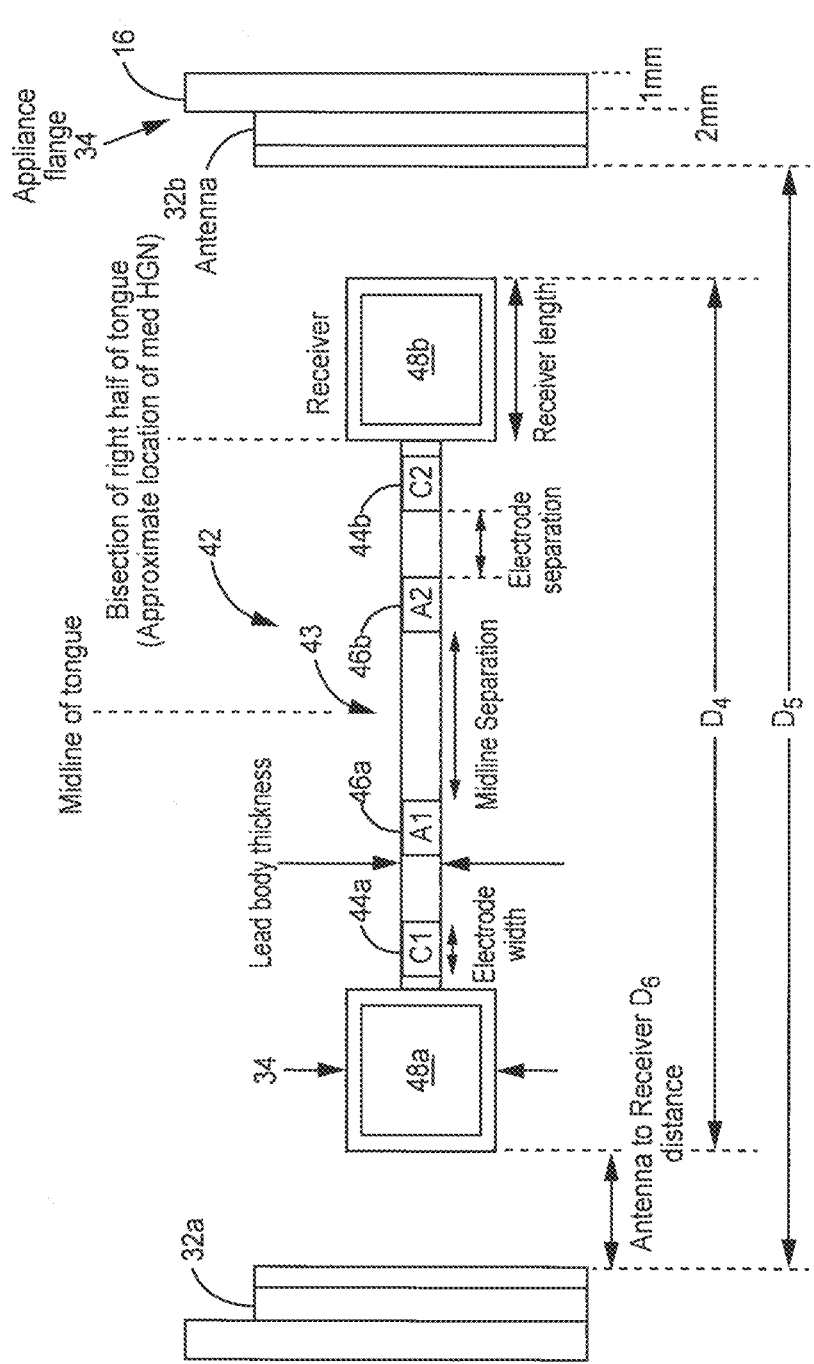
FIG. 2 is a schematic diagram illustrating an example removable oral device and lead configuration positioned between an antenna and a mounting retainer.

FIGS. 1-2 are schematic diagrams illustrating an example configuration of a dental system 10 for repeatedly delivering electrical neural stimulation to cause a patient's tongue to move away from the air passageway in order to reduce or eliminate obstructive sleep apnea (OSA). Dental system 10 comprises a percutaneously placed lead 42, a removable flexible component 16 (also referred to as a "mounting retainer" or "polymeric portion" shown in FIG. 3) that is not mechanically connected to the lead 42, one or more electrical stimulators 30 mounted onto the flexible component 30 through shrink wrapped polymeric material 34 that partially or fully covers the electrical stimulator 30 and at least a portion of the flexible component 16. Exemplary thickness of polymeric material 34 or encapsulation thickness can be up to 0.55 mm or up to 1 mm.

Medical electrical lead 42 can comprise any type of lead that includes one or more electrodes along the lead body 43 to allow electrical stimuli (e.g. pulses) to be delivered to neural tissue such as the hypoglossal neural tissue. An exemplary lead body thickness can be 1.27 mm. Lead body 43 extends along a longitudinal axis 25 between first and second ends 27a,b, as shown in FIGS. 1-2, and FIGS. 5-6 which are located between receivers 48a,b. One or more electrodes 46a,b are positioned along the lead body 43 between a first and second contact electrodes 44. As shown, preferably electrodes are positioned adjacent to receivers 48a,b. In one embodiment, electrodes 46a,b can be configured to serve as anodes while electrodes 44 serve as cathodes, or vice versa. In one or more embodiments, each cathode is paired with an anode spaced closest to that cathode. The electrodes 46a,b may be circular (e.g., ring) electrodes surrounding the lead body 43, conformable electrodes, segmented electrodes, or any other type of electrodes capable of forming unipolar, bipolar or multipolar electrode configurations for therapy. In general, ring electrodes can be arranged at different axial positions along the length of lead 42.

Figure 31:
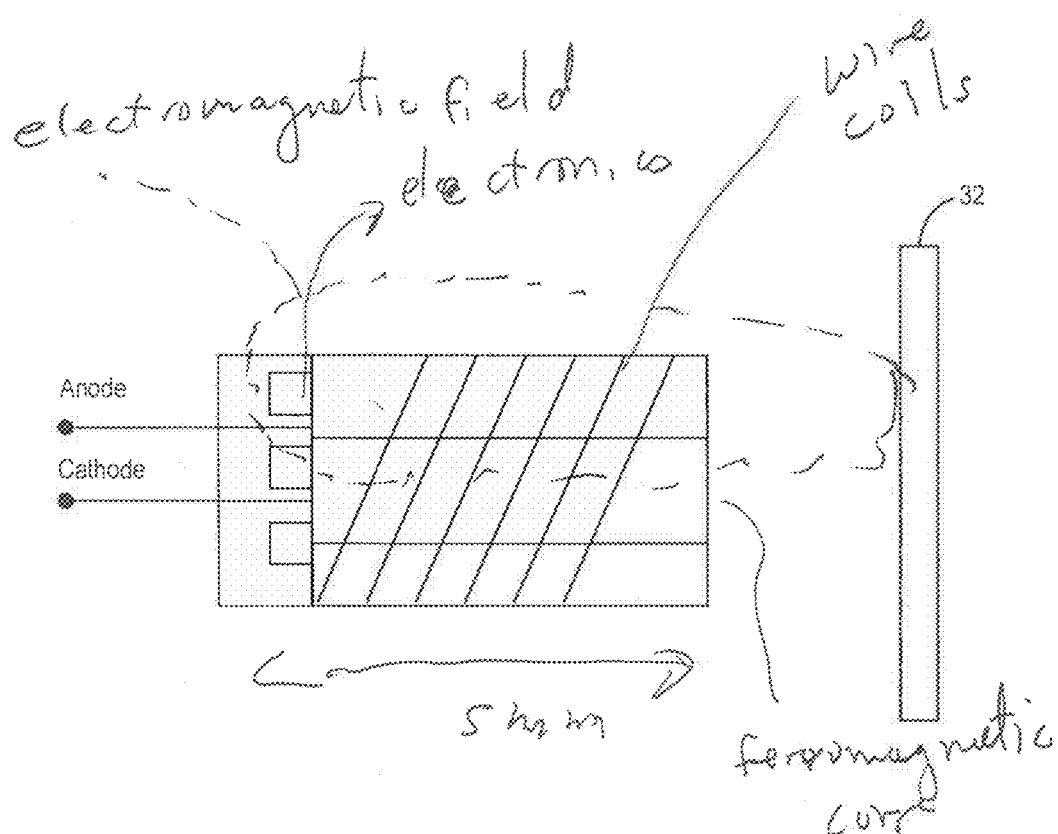
FIG. 31 is a schematic diagram of a receiving antenna.

Receivers 48a,b, (also referred to as receiving transmitters or non-contact receivers) located at each end of lead 42, are configured to receive or acquire electrical signals from the pulse generator 70 (also referred to as, or related to, as a stimulation generator) via the transmitting antenna. Receivers 48a,b, in turn, conduct the electrical signals to electrodes 46a,b. Receivers 48a,b receive electrical signals from the electrical stimulator 30 but do not serve as a tissue stimulating electrode. FIG. 31 depicts an exemplary receiving antenna 48a,b. receiving antenna 48a, comprises a ferromagnetic core which is a magnet to help with the electromagnetic field that passes through the winds. The varying fields produces a voltage.

Figure 3:
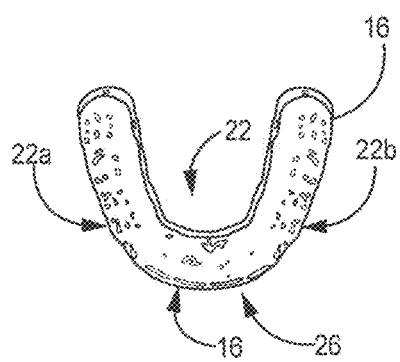
FIG. 3 is a schematic diagram of an example polymeric component configured to fit over a set of teeth.
Figure 4:
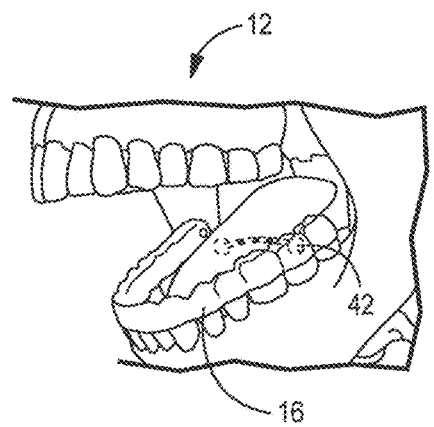
FIG. 4 is a schematic diagram illustrating the teeth of the lower jaw onto which the polymeric component of FIG. 3 will be placed.

FIGS. 1 and 3 show flexible component 16 comprises a polymer that forms a shell over a set of teeth for a patient. Flexible component 16 can be made using any conventional technique associated with a retainer or braces. Exemplary polymers used to form component 16 comprise any one of the polymers used for creating conventional retainers or braces for teeth. Flexible component 16 includes an anterior portion 18, a posterior portion 20, first and second side portions 22a,b, all of which further include inner 22 and outer surfaces 26a,b respectively. Typically, flexible component 16 is inserted or snapped into position over the patient's lower set of teeth, as shown in FIG. 4. The patient positions the flexible component 16 over the first, second, third molars 36, 38, 40, respectively and the front lower teeth and pushes the flexible component 16 directly down until a click or snapping sound is heard. To fit, flexible component 16 is configured to fit each tooth like a hand in glove by ensuring adequate space between teeth. Flexible component 16 is configured to have sufficient distances between teeth, as shown in FIG. 1. For example, D1 represents the between the right and left antenna 32 at the level of the third molar 40 whereas D2 represents the distance between the first and third molars 36, 38. D3 is the distance between the outside surfaces on the inside of the mouth of the left and right antenna 32. D4 is the distance from one end of the first receiver 48a to the other end of the other receiver 48b. D5 is the distance between the first and second antennas 32a,b. D6 is the distance between the antenna 32a and the receiver 48a.

FIGS. 25-29 depict exemplary transmitting antenna 32a,b designs that may be employed to transmit energy to transmit receivers 48a,b (also referred to as receivers). Generally, the transmitter and receiver antenna are configured to result in complete (i.e. 100%) or substantially complete (90% or more) in power transfer efficiency and 50% increase in load voltage. To achieve the design goals, the transmitter antenna is configured to (1) increase its outer diameter to 14 mm, (2) increase copper diameter to 0.3 mm or about 0.3 mm, and (3) set an inner coil diameter at 3.9 mm or about 3.9 mm. Transmitting antenna coil designs are formed in a variety of shapes.

Preferably, a substantially rectangular transmitter 400 is employed to transmit energy to receivers 48a,b. Substantially rectangular transmitter 400 ranges from about 85 to 99% in power transfer efficiency a rectangular shape. Transmitter 400 includes a coil 404 disposed onto a polymeric substrate 404 thereon. The coil 404 is wrapped around itself to form four coils aligned next to each other. In one embodiment, a copper coil is employed having 28 AWG or 0.32 mm. The copper coil can have a diameter of 0.3 millimeters (mm) with a 6.35 mm×16.3 mm dimension.

Figure 26:
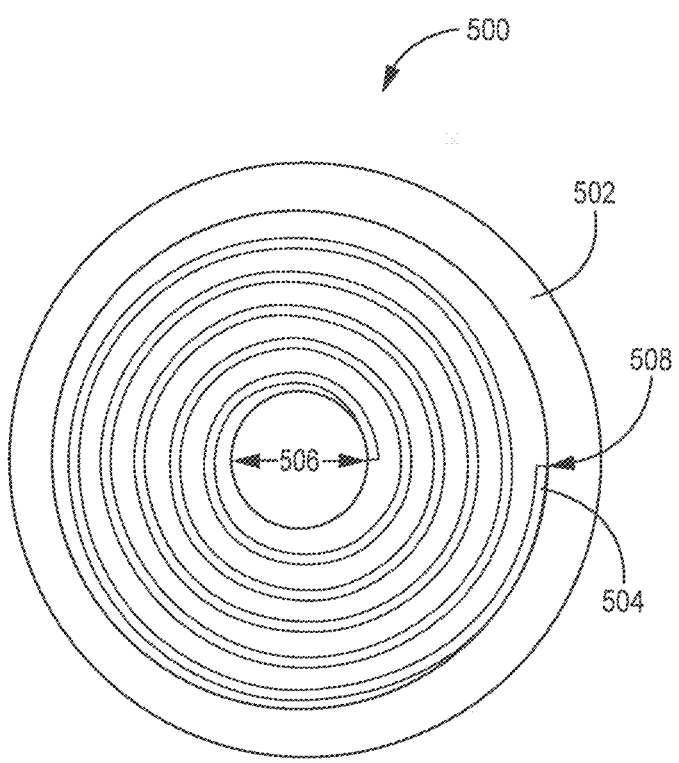
FIG. 26 is a schematic diagram of a substantially circular transmitter coil design.

FIG. 26 comprises a substantially circular transmitter coil 500 having a polymeric substrate 502 with a coil 504 placed thereon. The coil starts at 506 and is wrapped about itself six times until the coil 504 is closer to the outer surface as opposed to its starting point. In one embodiment, a copper coil is employed having 28 AWG or 0.32 mm. The copper coil can have a diameter of 0.3 mm with an inner coil diameter 506 comprising 3.9 mm. The outer coil diameter extends 14 mm. Additionally, each wind is shown to be spaced apart. The total coil diameter 508 extends from a central starting point to an outer end point of the wire.

Figure 27:
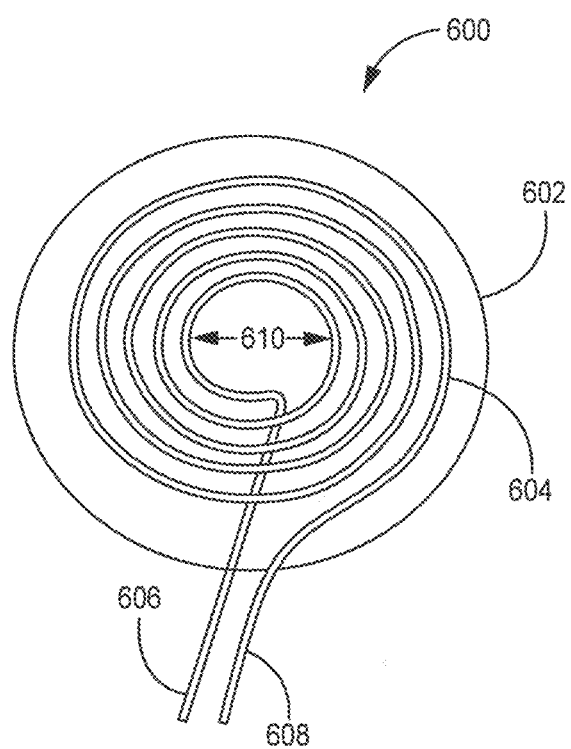
FIG. 27 is a schematic diagram of yet another embodiment of a circular transmitter coil design.

FIG. 27 comprises a substantially circular transmitter coil 600 having a polymeric substrate 602 with a coil 604 placed thereon. The copper coil starts at 606 and is wrapped about itself five times until the coil 604 is closer to the outer surface as opposed to its starting point. In one embodiment, a copper coil is employed having 28 AWG or 0.32 mm. The copper coil can have a diameter of 0.3 millimeters (mm) with an inner coil diameter 610 comprising 3.9 mm. The outer coil diameter extends 14 mm. Additionally, each wind is shown to be spaced apart. The end 608 of the wire is shown in FIG. 27.

Figure 28:
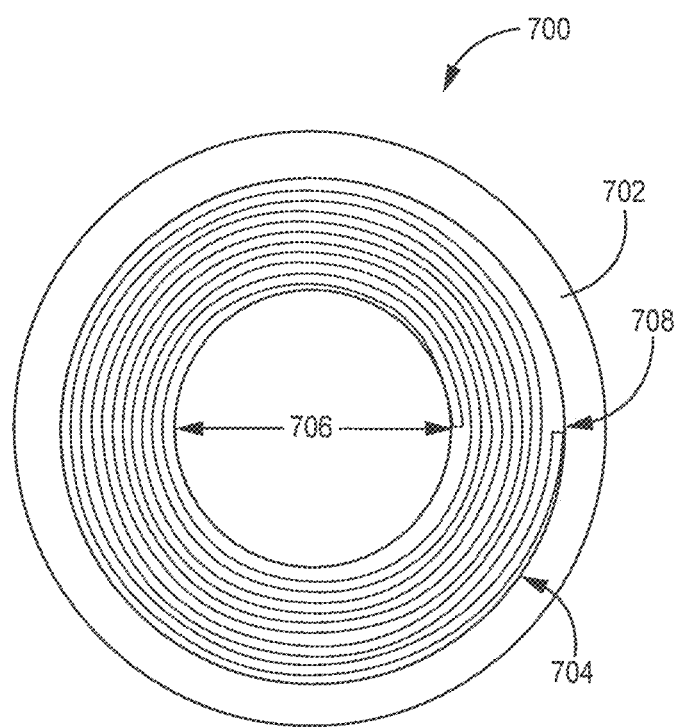
FIG. 28 is a schematic diagram of still yet another embodiment of a circular transmitter coil design.

FIG. 28 comprises a substantially circular transmitter coil 700 having a polymeric substrate 702 with a coil 704 placed thereon. The coil starts at 706 and is wrapped about itself five or six times until the coil 704 is closer to the outer surface as opposed to its starting point. The winds are much closer together than the winds of FIG. 27. In one embodiment, a copper coil is employed having 28 AWG or 0.32 mm. The copper coil can have a diameter of 0.3 millimeters (mm) with an inner coil diameter 706 comprising 3.9 mm. The outer coil diameter extends 14 mm. Additionally, each wind is shown to be spaced apart. The end 708 of the wire is shown in FIG. 28.

Figure 29:
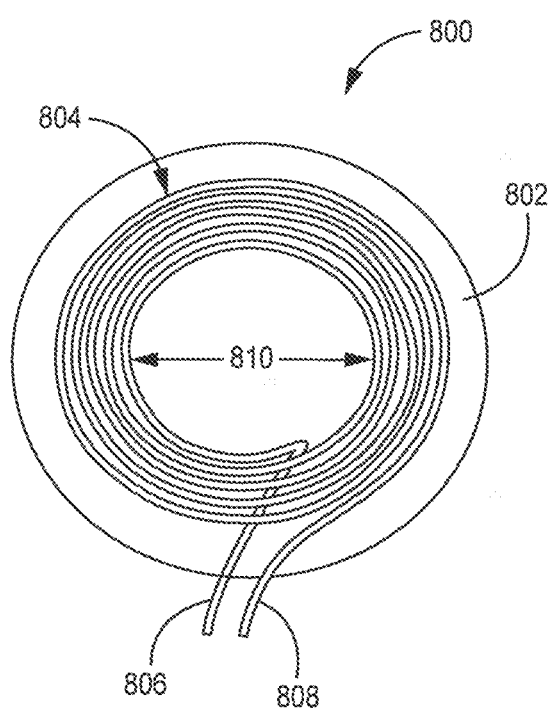
FIG. 29 is a schematic diagram of still yet another embodiment of a circular transmitter coil design.

FIG. 29 comprises a transmitter coil 800 with a circular head. Transmitter coil 800 comprises a polymeric substrate 802 with a coil 804 placed thereon. The coil starts at 806 and is wrapped about itself six times until the coil 804 is closer to the outer surface as opposed to its starting point. In one embodiment, a copper coil is employed having 28 AWG or 0.32 mm. The copper coil can have a diameter of 0.3 millimeters (mm) with an inner coil diameter 810 comprising 3.9 mm. The outer coil diameter extends 14 mm.

The electrical stimulator 30 operates in conjunction with a percutaneously implanted lead 42 to stimulate one or both of the hypoglossal nerves in order to move the tongue in such a manner that the tongue is prevented from blocking the air passageway. Electrical stimulation of both the hypoglossal nerves occur so that the tongue is more easily moved. In one or more embodiments, bilateral stimulation means that during the time in which one hypoglossal nerve is stimulated, the other hypoglossal nerve is also stimulated. In one or more other embodiments, both hypoglossal nerves are stimulated at the same time for patients where the response is limited. In one or more embodiments, stimulation can be delivered to neural tissue near one hypoglossal nerve at a time to avoid muscle fatigue. Stimulation energy can be simultaneously, or about simultaneously, delivered from electrical stimulator 30 to the hypoglossal nerves of patient 12 via one or more electrodes 46a,b or 44a,b of implantable lead 42. The external stimulator 30 is mounted on flexible component 16.

Preferably, the electrical stimulator 30 can be positioned in the buccal region of the mouth which is the outer surface of the mounting retainer between the cheek and the lower set of teeth. Optionally, the electrical stimulator 30 can be positioned between the lower set of teeth and the tongue.

In exemplary embodiments, electrical stimulator 30 delivers stimulation therapy according to one or more programs. A program defines one or more parameters that define an aspect of the therapy delivered by electrical stimulator 30 according to that program. For example, a program that controls delivery of stimulation by electrical stimulator 30 in the form of pulses may define a voltage or current pulse amplitude, a pulse width, a pulse rate, and an electrode combination (e.g., combination of electrodes and polarities) for stimulation pulses delivered by electrical stimulator 30 according to that program. Moreover, therapy may be delivered according to multiple programs, wherein multiple programs are contained within each of a plurality of groups. In some cases, stimulation pulses formulated according to parameters defined by different programs may be delivered on a time-interleaved basis or other time-ordered basis.

Figure 12:
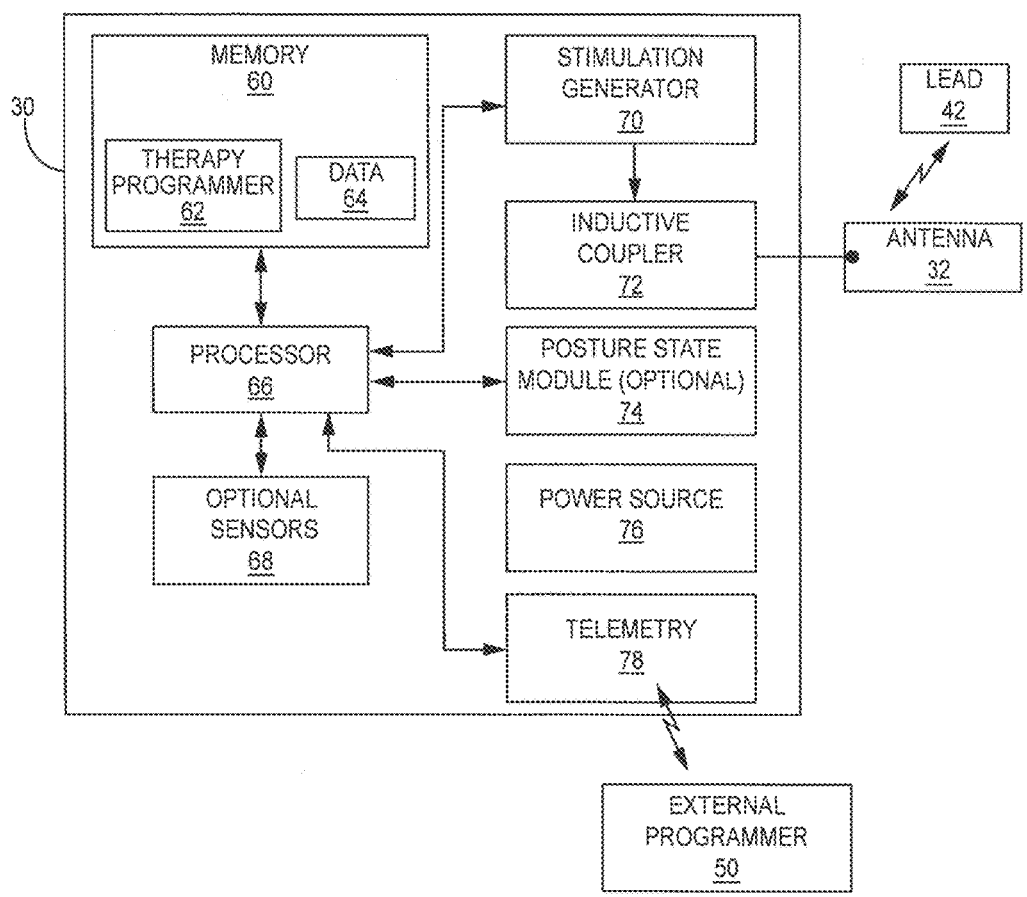
FIG. 12 is a functional block diagram illustrating an example configuration of various components of an external neurostimulator used in the system shown in FIG. 1 to stimulate one or both hypoglossal nerves.

FIG. 12 is a functional block diagram illustrating various components of an external stimulator 30. In the example of FIG. 12, external stimulator 30 includes a processor 66, memory 60, stimulation generator 70, an inductive transmitter or coupler 72, a posture state module 74 (optional) and/or other sensors, a power source 76 and optionally a telemetry circuit 78 as described in U.S. patent application Ser. No. 12/433,632, entitled "GENERATION OF SLEEP QUALITY INFORMATION BASED ON POSTURE STATE DATA" incorporated by reference in its entirety. Inductive transmitter 72 is configured to perform wireless energy transmission.

Memory 60 stores instructions (e.g. therapy programmer 62) for execution by processor 66, stimulation therapy data 64, posture state information, and any other information regarding therapy or patient 12. Therapy information may be recorded for long-term storage and retrieval by a user, and the therapy information may include any data created by or stored in memory 60. Memory 60 may include separate memories for storing instructions, posture state information, program histories, and any other data that may benefit from separate physical memory modules. For example, other data saved in memory may include historical data. Historical data is acquired from the patient when the patient is sleeping. The historical data can be data that indicates how long on average the patient takes before falling asleep. In addition or alternatively, sounds can be acquired with a microphone that is indicative of sleeping versus when the patient is awake.

Processor 66 controls stimulation generator 70 to deliver electrical stimulation via electrode combinations formed by electrodes. For example, stimulation generator 70 delivers electrical stimulation therapy via electrodes on lead 42, e.g., as stimulation pulses or continuous waveforms. Components described as processors for external stimulator 30, external programmer 50 (FIG. 1) or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. Additionally, processor 66 can comprise a single processor connected to two different electrical stimulators 30 or two separate processors may be separately connected to each electrical stimulator 30. Additionally, processor 66 controls when each electrical stimulator 30 delivers an electrical signal to a tissue site. Processor 66 is configured to alternately generate control signals to an electrical stimulator 30 to deliver and electrical signal.

Stimulation generator 70 may include stimulation generation circuitry to generate stimulation pulses or waveforms and switching circuitry to switch the stimulation across different electrode combinations, e.g., in response to control by processor 66. In particular, processor 66 may control the switching circuitry on a selective basis to cause stimulation generator 70 to deliver electrical stimulation to selected electrode combinations and to shift the electrical stimulation to different electrode combinations. Stimulation generator may include a pulse generator, instructions and/or circuitry related to the pulse generator.

An electrode configuration, e.g., electrode combination and associated electrode polarities, may be represented by a data stored in a memory location, e.g., in memory 60, of external stimulator 30. Processor 66 may access the memory location to determine the electrode combination and control stimulation generator 70 to deliver electrical stimulation via the indicated electrode combination. To change electrode configurations, amplitudes, pulse rates, or pulse widths, processor 66 may command stimulation generator 70 to make the appropriate changed to therapy according to instructions within memory 60 and rewrite the memory location to indicate the changed therapy. In other embodiments, rather than rewriting a single memory location, processor 66 may make use of two or more memory locations.

When activating stimulation, processor 66 may access not only the memory location specifying the electrode combination but also other memory locations specifying various stimulation parameters such as voltage or current amplitude, pulse width and pulse rate. Stimulation generator 70, e.g., under control of processor 66, then makes use of the electrode combination and parameters in formulating and delivering the electrical stimulation to patient 12. While stimulation pulses are described, stimulation signals may be of any of a variety of forms such as sine waves or the like. Exemplary stimulation parameters are provided below. Pulse Rate can be between approximately 0.5 Hz and 1200 Hz, more preferably between approximately 5 Hz and 250 Hz, and still more preferably between approximately 30 Hz and 40 Hz. Most preferably, the pulse rate is at or about 40 Hz.

Amplitude can be between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

Pulse Width can be between about 10 microseconds and 5000 microseconds, more preferably between approximately 100 microseconds and 1000 microseconds, and still more preferably between approximately 40 microseconds and 450 microseconds.

In one or more embodiments, electrical stimulation is preferably delivered as bipolar stimulation. In one or more embodiments, stimulation is delivered using the following parameters and/or components:

An exemplary rechargeable battery is described in U.S. Pat. No. 9,077,022, entitled LITHION-ION BATTERY, assigned to the assignee of the present invention, the disclosure of which is incorporated by reference in its entirety. In the event that the battery requires recharging, an external lead or inductive coupling device (not shown) may be used to electrically couple the battery to a charging device or apparatus. Exemplary battery requirements include, 400 mW, 100 mWhr, 10% transfer efficiency, 10 Whr battery duty cycle: 10 hrs, 500 ohms, 40 Hz, and 5 V.

In one or more embodiments, external stimulator 30 delivers stimulation using the following parameters 1.5 volt at 510 microseconds and 30 hertz (Hz). Processor 66 stores stimulation parameters in memory 60, e.g., as programs and groups of programs. Upon selection of a particular program group, processor 66 may control stimulation generator 70 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation.

Figure 13:
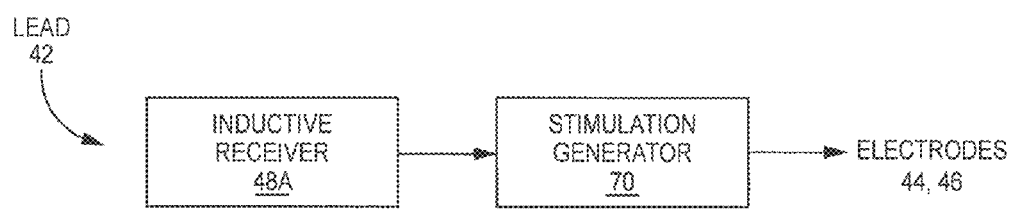
FIG. 13 is a schematic diagram of a portion of a stimulation lead which includes energy receivers and stimulating electrodes.

As applied to the present disclosure, processor 66 sends a control signal to stimulation generator 70 to produce stimulation (e.g. waveform or pulses). In response to the signal, the stimulation generator sends a stimulation signal to the inductive coupler 72 which in turn transmits the stimulation signal to the lead through antenna 32. Referring to FIG. 13, the stimulation signal is received by the receivers 48*a,b* which then sends the signal to the stimulation generator 70. The stimulation generator 70 sends electrical pulses to the electrodes 44, 46 on the lead 42.

Figure 24:
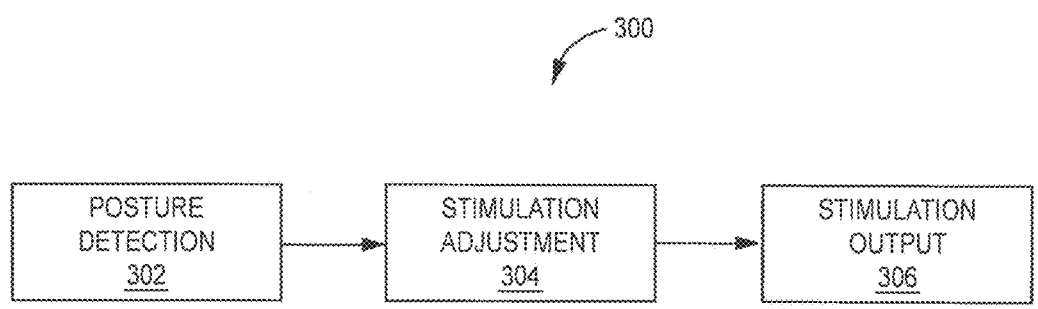
FIG. 24 is a block diagram of stimulation output in response to posture detection.
Figure 25:
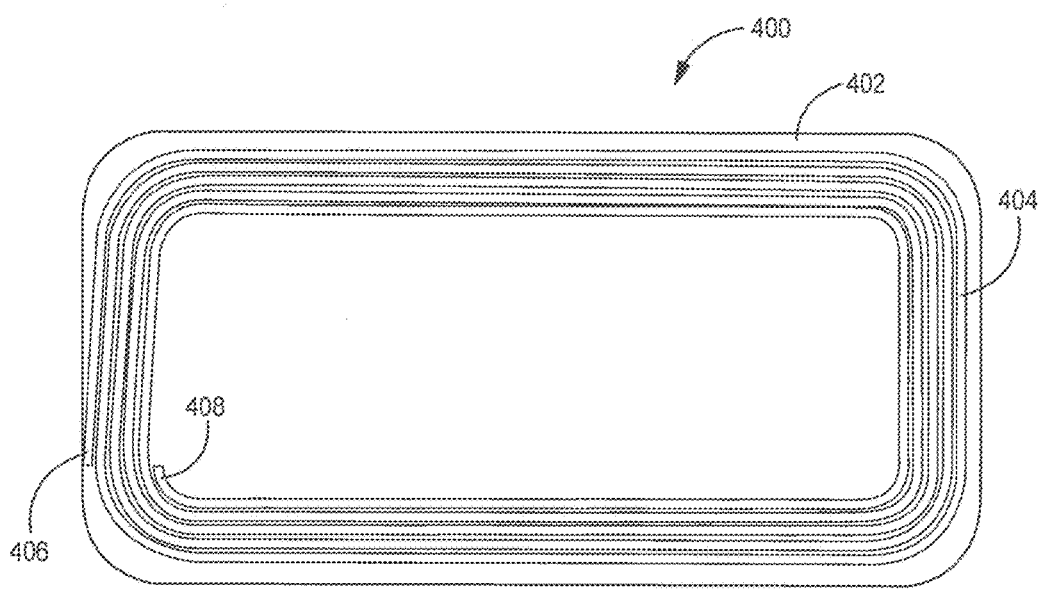
FIG. 25 is a schematic diagram a rectangular transmitter coil design.

Posture state module 74 allows external stimulator 10 to sense or detect at block 302 of FIG. 24 the patient posture state, e.g., posture, activity or any other static position or motion of the patient. In the example of FIG. 12 and FIG. 24, posture state module 74 may include one or more posture state sensors, e.g., one or more accelerometers such as three-axis accelerometers, capable of detecting static orientation or vectors in three-dimensions. The three-axis accelerometer may be a micro-electro-mechanical accelerometer. In other examples, posture state module 74 may alternatively or additionally include one or more gyroscopes, pressure transducers or other sensors to sense the posture state of patient. Posture state information generated by posture state module 74 and processor 66 may correspond to an activity, posture, or posture and activity undertaken by patient or a gross level of physical activity, e.g., activity counts based on footfalls or the like. For example, at block 304 of FIG. 24, electrical stimulation delivered to one or more tissue sites from lead 42 can be adjusted in response to detection of the patient's posture. At block 306, the processor of the electrical stimulator 30 automatically adjusts the electrical stimulation to be delivered. In response to the stimulation adjustment at block 304, the electrical stimulation is delivered or outputted to the one or more neural tissues is activated or deactivated. For example, if a person is lying down for 30 minutes, the electrical stimulator may turn on. In one or more embodiments, additional data to posture data may be required to activate electrical stimulation. For example, electrical stimulation may not be delivered until the patient's posture data and sound data is detected. To detect sound, a microphone or other sensor may be used to sense the sleep state of a patient. A microphone can be placed in the housing or can of the electrical stimulator 30 or on the mounting retainer 16.

Optionally, dental system 10 (FIG. 1 and FIG. 26) can include posture detection with placement of a three axis accelerometer placed in a device 14 or stimulator 30. The accelerometer can be on one of the flexible circuits that reside in the pulse generator or retainer. To ensure continued effective therapy due to posture state changes, electrical stimulator 30 may include a posture state module that detects the posture state of patient 12 and causes the electrical stimulator 30 to automatically adjust stimulation according to the detected posture state. In response to a posture state indication by the posture state module, electrical stimulator 30 may change program group, program, stimulation amplitude, pulse width, pulse rate, and/or one or more other parameters, groups or programs to maintain therapeutic efficacy. When a patient rolls over, for example, electrical stimulator 30 may automatically start and/or increase stimulation amplitude so that patient 12 does not need to manually adjust stimulation amplitude. In one or more embodiments, electrical stimulator 30 or ramp up in gradations until a preset level is established.

In addition, stimulation output may also be adjusted with the use of a microphone or other sensor to detect sounds or vibration in dental system 10 or stimulator 30. The microphone is configured to detect snoring and/or other sleep sounds which will determine when patient is asleep, the depth of sleep, and if the upper airway is causing an apneic event.

A user, such as the patient 12, can manually adjust inputting settings on the electrical stimulator 30, as described in Medtronic's Patient Programmer Model 37642, incorporated by reference in its entirety. From this manual, the patient may make limited programming changes such as small changes in output amplitude and pulse width. The manual also describes how the patient can turn the therapy on and off or to set timers to turn the therapy on or off.

In one or more embodiments, a user, such as a clinician or patient 12, optionally interacts with a user interface of an external programmer 50 (FIG. 12) to program external electrical stimulator 30. Physician Programmer Model 8840 available from Medtronic and incorporated by reference in its entirety can be used by the physician to program the device for delivering electrical stimulation.

Programming of electrical stimulator 30 may refer generally to the generation and transfer of commands, programs, or other information to control the operation of electrical stimulator 30. For example, external programmer 50 may transmit programs, parameter adjustments, program selections, group selections, or other information to control the operation of electrical stimulator 30, e.g., by wireless telemetry. As one example, external programmer 50 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis. These programs may adjust output parameters or turn the therapy on or off at different time intervals.

In some cases, external programmer 50 may be characterized as a physician or clinician programmer if it is primarily intended for use by a physician or clinician. In other cases, external programmer 50 may be characterized as a patient programmer if it is primarily intended for use by a patient. A patient programmer 50 is generally accessible to patient 12 and, in many cases, may be a portable device that may accompany the patient throughout the patient's daily routine. In general, a physician or clinician programmer may support selection and generation of programs by a clinician for use by stimulator 30, whereas a patient programmer may support adjustment and selection of such programs by a patient during ordinary use.

External programmer 50 may present posture state data stored in electrical stimulator 30 from the detected posture states of patient 12, as described in patent application Ser. No. 12/433,632, entitled "GENERATION OF SLEEP QUALITY INFORMATION BASED ON POSTURE STATE DATA" and incorporated by reference in its entirety.

To produce posture information, electrical stimulator 30 or an external programmer 50 may then analyze the stored posture state data over the length of the applicable time interval, i.e., the applicable therapy session. To calculate an average number of patient therapy adjustments for a given posture state over a period of time, for example, electrical stimulator 30 or programmer 50 divide the number of patient therapy adjustments detected in the therapy session by the number of applicable time periods in the therapy session.

Alternatively external programmer 50 may present sleep sound data stored in electrical stimulator 30 from the detected posture states of patient 12. Additionally or alternatively, the time in which the patient is lying down can be acquired and a history of such data can be stored into memory.

Generally, the dental system 10, described above, is used to stimulate the hypoglossal nerve(s) by placement of one or more electrodes 44a,b or 46a,b located near the back of the first molar and the base of the tongue. Alternatively, the electrodes can be placed in other muscles of the upper airway that may lose tone during sleep causing the upper airway collapse.

The target tissue (e.g. neural tissue, muscle) may be any tissue affected by electrical stimulation energy (e.g. electrical stimulation pulses or waveforms) for moving a portion of the tongue. Such tissue may include nerves, smooth muscle, and skeletal muscle. In the example illustrated in FIG. 9 herein, the exemplary target tissue involves the hypoglossal nerves disposed in or near the tongue. The anatomy of the tongue is described in detail in Three-Dimensional Atlas of Human Tongue Muscles, THE ANATOMICAL RECORD 296:1102-1114 (2013), which is incorporated herein by reference in its entirety. Generally, the tongue comprises a base, a body, and a blade.

The base 87 is posterior to the sulcus terminalis which comprises circumvallate papillae taste receptors. The body of the tongue involves the anterior part of the genioglossus (GG) muscle 90. In particular, the body extends from the circumvallate papillae to a frenulum. The blade is the region of the tongue anterior to the frenulum. The body, the largest segment, includes an anterior and posterior portion. The anterior portion is inferior to the hard palate while the posterior body lies inferior to the soft palate.

The GG muscle 90, which composes the bulk of the midtongue posterior to the frenulum, are paired muscles that originate from the inner midline of the mandible and fan out in a 90 degree arc. The GG muscle 90 protrudes and depresses the tongue. Tongue protrusion is caused by horizontal compartment and the posterior fascicles of an oblique compartment. Depression of the body of the tongue is caused by the more vertically oriented fascicles in the middle of the oblique GG muscle 90, ventroflexion and possibly retrusion of the tongue tip by the most anterior muscle fascicles.

The hyoglossus (HG) 92 originates from the tongue body and greater cornu of the hyoid bone. The HG 92 is bordered by the GG muscle 90, the inferior longitudinal (IL) muscle medially and the styloglossus (SG) muscle 94 laterally. The HG 92 is a thin planar muscle near its origin but separates into distinct fascicles that fan out and insert along the length of the tongue. The action of the HG 92 is retrusion and depression of the lateral margin of the tongue.

The SG 94 is the most lateral of the tongue muscles. The SG 94 generally comprises posterior and anterior compartments. The smaller posterior compartment merges into and possibly passes through the lateral surface of the HG muscle 92 at the tongue base while a larger anterior compartment courses along the lateral aspect of the and merges with the IL muscle and other muscles to form the combined longitudinal muscle. The action of the SG 94 is retrusion and elevation of the lateral margin of the tongue. Specifically, the SG pulls the sides of the tongue upwards toward the roof of the mouth. The geniohyoid 96 protrudes the tongue.

Figures 7, 8:
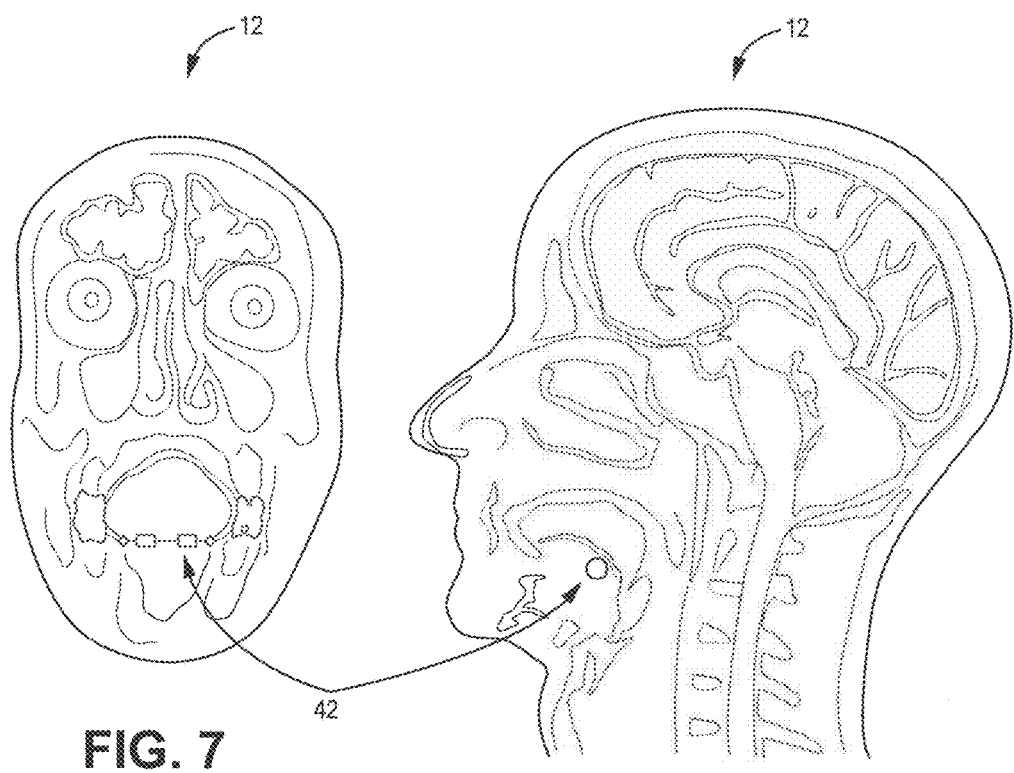
FIG. 7 depicts a cross-sectional coronal plane view of a human head with a lead implanted in the base of the tongue.
FIG. 8 depicts a cross-sectional sagittal view of a human head with a lead implanted in the base of the tongue.
Figure 9:
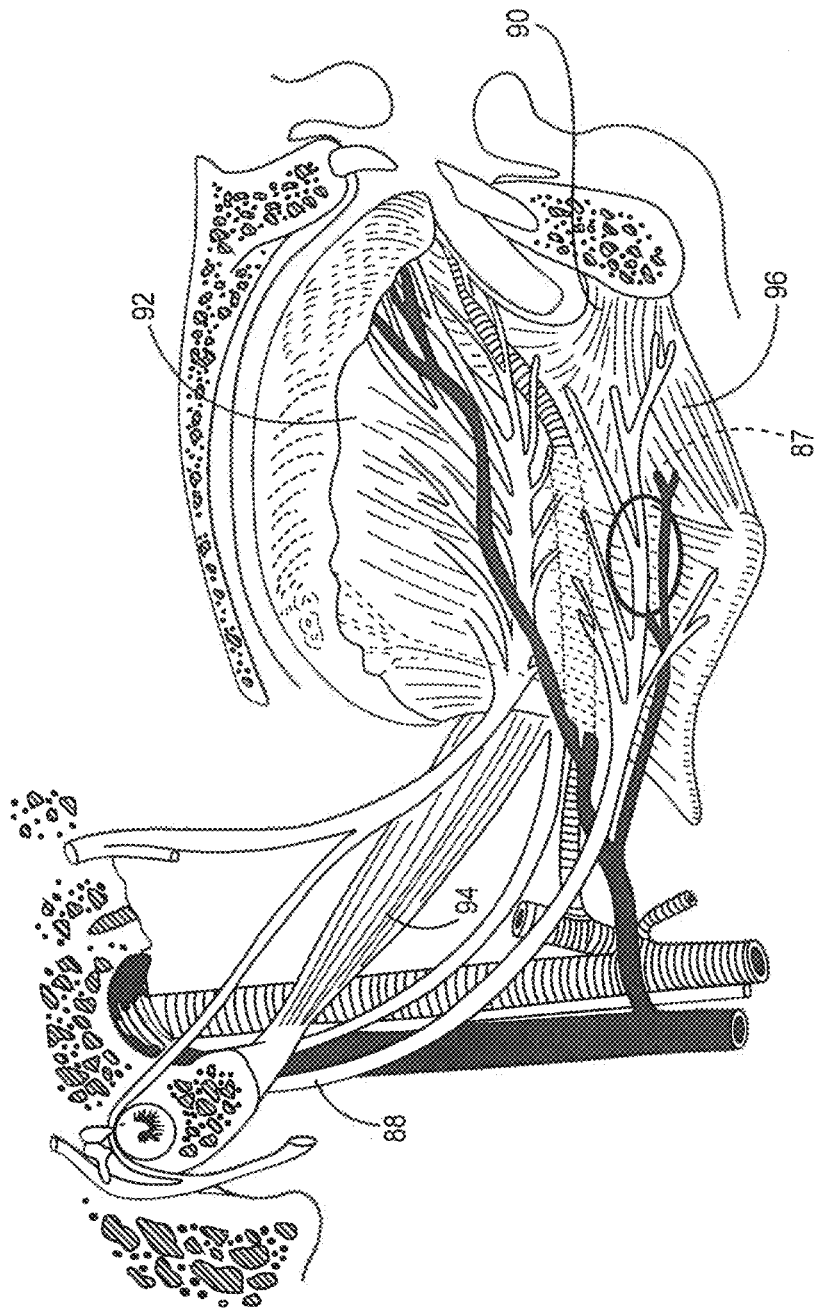
FIG. 9 depicts a cross-sectional sagittal view of a patient's jaw with the implant location of a lead indicated through a base of a tongue proximate the hypoglossal nerve.
Figure 10:
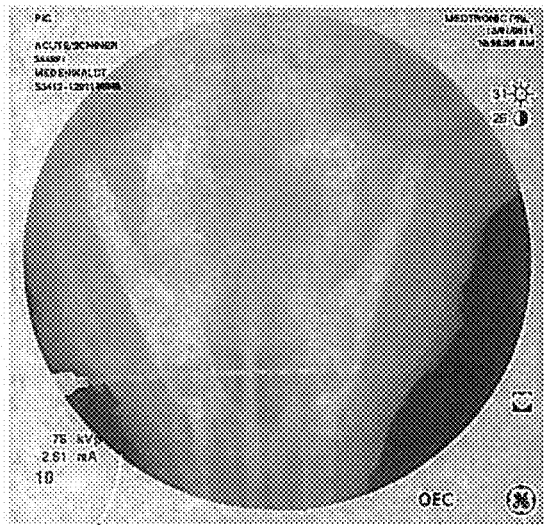
FIG. 10 is a fluoroscopic image showing a medical electrical lead being implanted through a needle in the base of the tongue of a pig.
Figure 11:
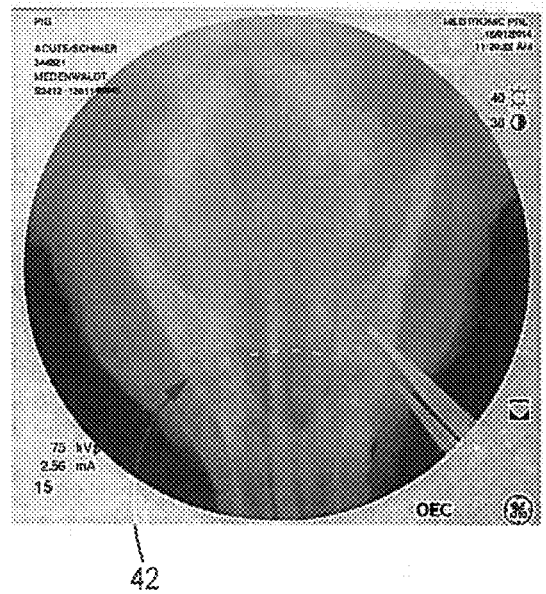
FIG. 11 is a fluoroscopic image showing a medical electrical lead implanted in the base of the tongue of the pig after the implant needle has been withdrawn.

The oral stimulation location by the pacing electrode(s) is shown in FIGS. 7 to 11. For example, FIG. 7 depicts a cross-sectional coronal plane view of a human head. FIGS. 8-9 depict a cross-sectional sagittal view of a human head with a lead implanted in the base of the tongue proximate the hypoglossal nerve. FIG. 10 is a fluoroscopic image showing a medical electrical lead being implanted through a needle in the base of the tongue of an animal while FIG. 11 is a fluoroscopic image showing a medical electrical lead implanted in the base of the tongue of an animal after the implant needle has been withdrawn.

The lead 42 is placed near the floor of the mouth and through the base of the tongue. The lead 42 is placed in the back of the mouth near the first molar. Lead 42 is inserted in or near the base of the tongue, which is perpendicular to the length of the tongue and the hypoglossal nerves that extend therethrough.

Figure 19:
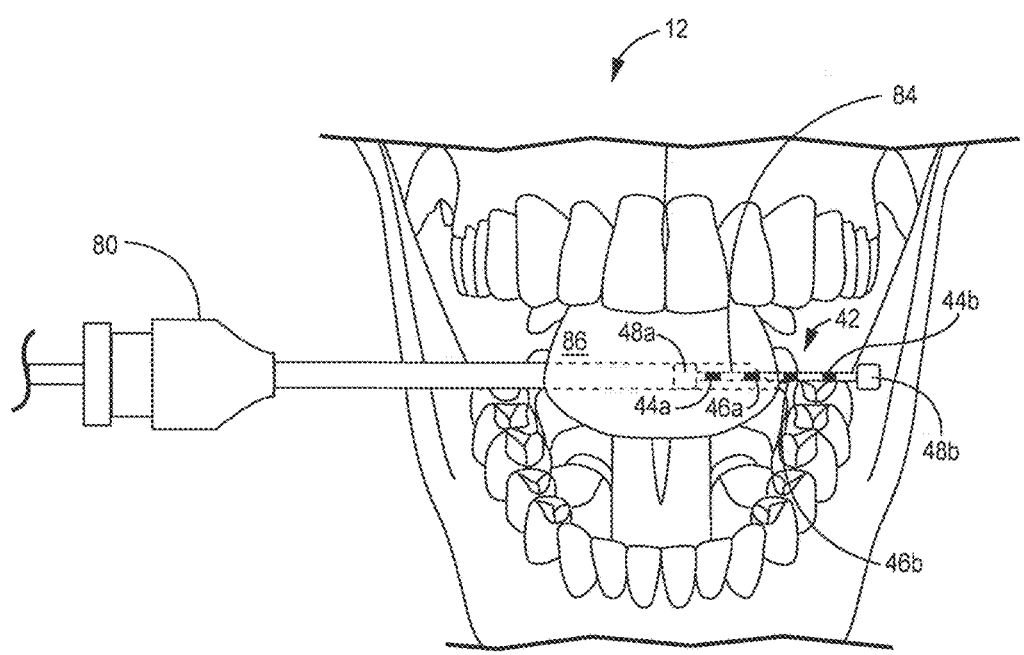
FIG. 19 is a schematic diagram of a front view of a distal end of the needle piercing a side of the base of the tongue while a lead is inserted inside a lumen of the needle on the opposing side of the needle.
Figure 20:
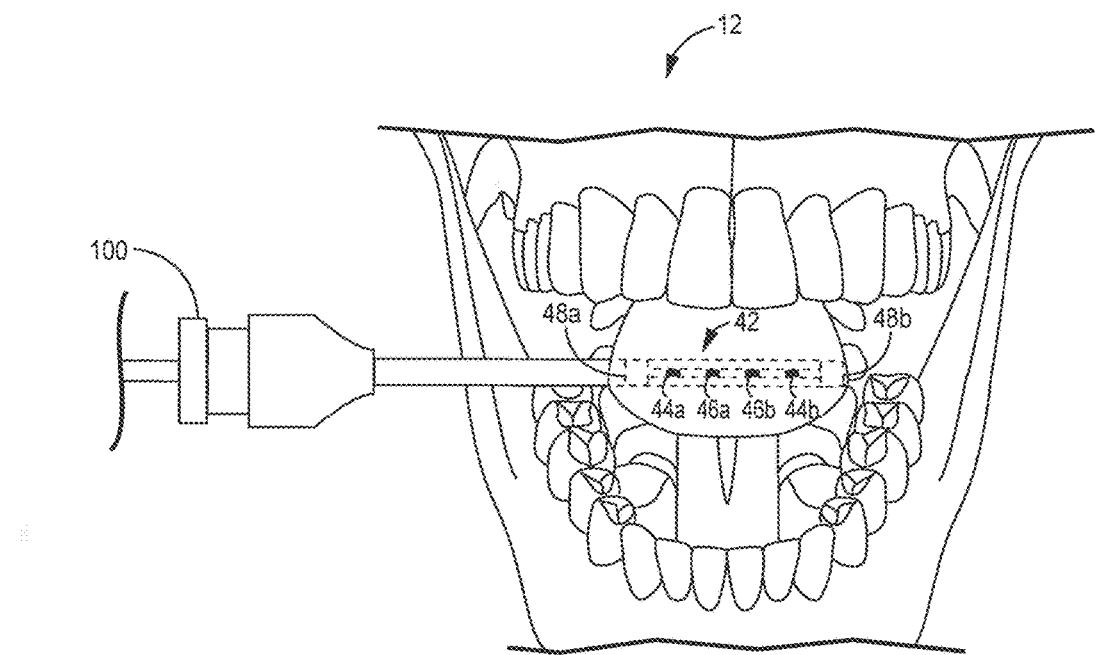
FIG. 20 is a schematic diagram of a front view of a distal end of the needle piercing a side of the base of the tongue while a lead is fully inserted inside a lumen of the needle on the opposing side of the needle.
Figure 21:
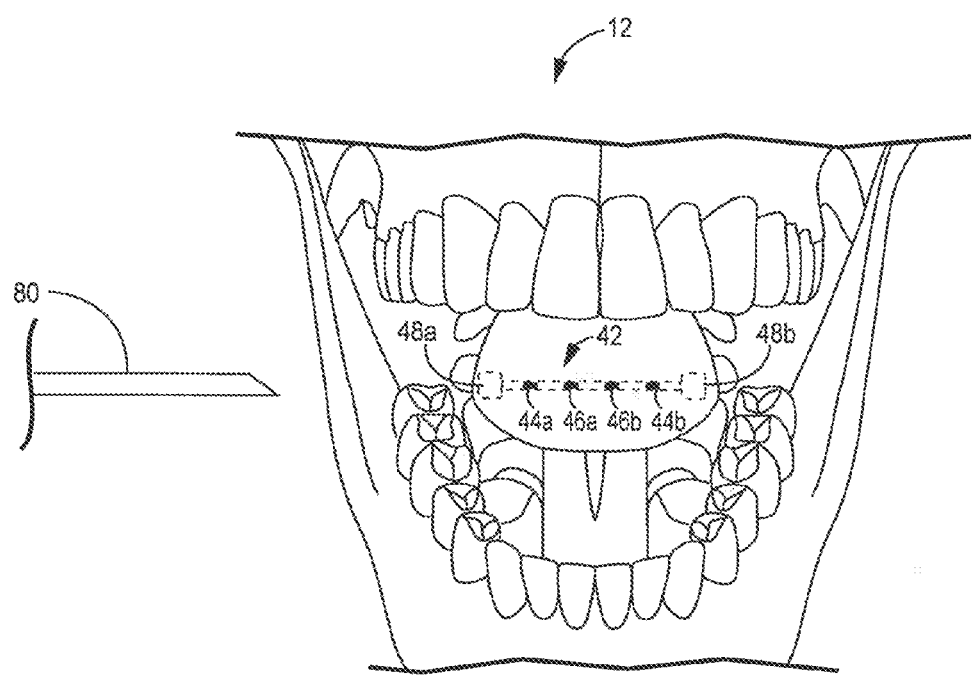
FIG. 21 is a schematic diagram of a front view of a distal end of the needle removed from the base of the tongue while a lead is fully inserted inside a lumen of the needle on the opposing side of the base of the tongue.
Figure 22:
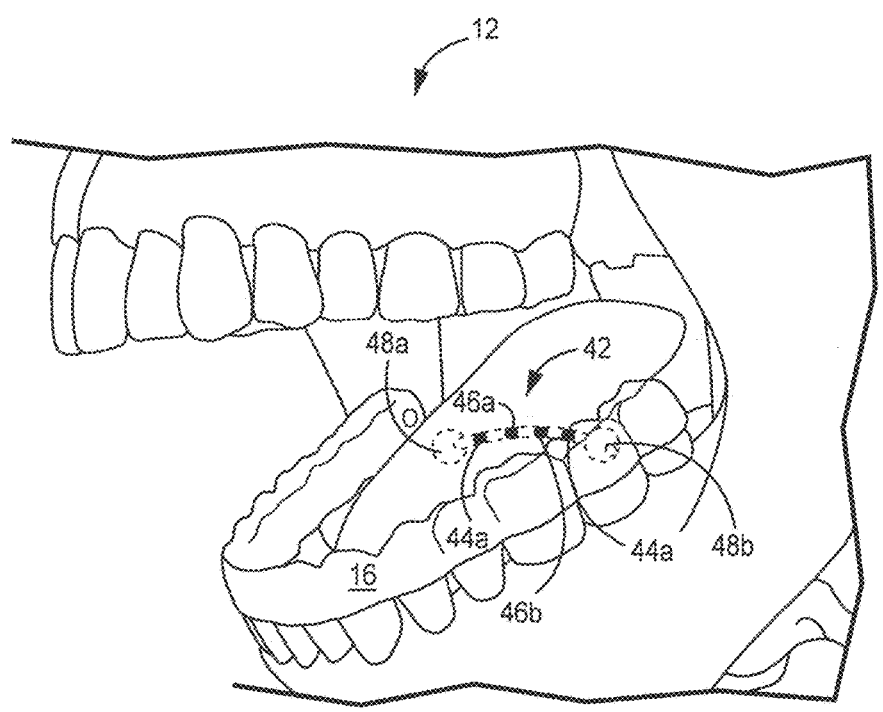
FIG. 22 is a schematic diagram of an oblique view of a lead implanted into the base of the tongue.

Referring to FIGS. 19-21, lead 42 includes first and second ends 8a,b that are inserted or implanted into the base of the tongue by a needle (e.g. 15 gauge needle etc.) that is introduced perpendicular to the longitudinal axis L of the tongue and passes into the base of the tongue. The lead 42 is particularly suitable for implantation to a base of the tongue using minimally invasive techniques, such as through a needle. The needle 80 includes a lumen sufficiently large in which a lead 42 is configured to reside and/or move longitudinally within the lumen, between the distal and proximal ends of the needle 80.

Figure 14:
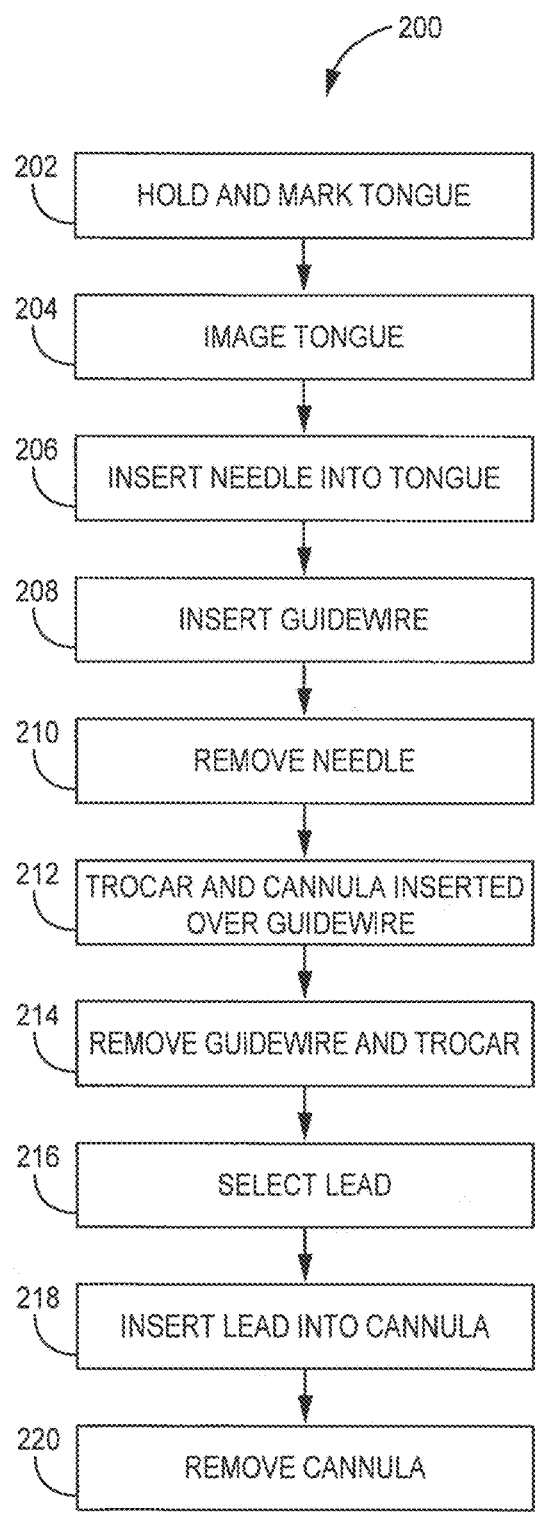
FIG. 14 is a flow diagram for placing a medical electrical lead into the musculature of the tongue.
Figure 15:
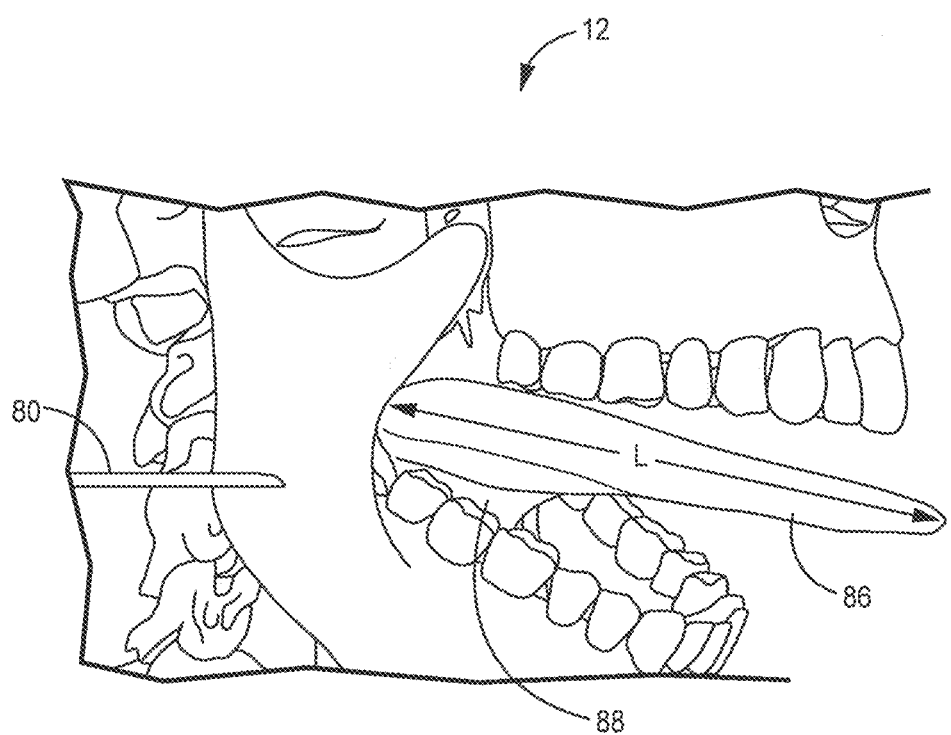
FIG. 15 is a schematic diagram of a needle positioned near a base of an extended tongue.

FIGS. 16-23 shows a portion of the steps of method 200 of FIG. 14 for implanting a lead 42 of a dental device system 10 into a base of a tongue to electrically stimulate the hypoglossal nerves. At block 202, the person implanting the lead gently extends and holds the tongue of the person receiving the lead 42. The implant site and exit site on the opposite side of the tongue is marked with a surgical marker. The patient's tongue is gently squeezed with forceps that includes sponges to comfortably hold the tongue. Optionally, block 204, to avoid puncturing an artery, ultrasound imaging can be used to identify the large artery and veins. At block 206, the needle (e.g. 18 gauge, 1.27 mm outer diameter (OD)) is inserted through the tongue such as through the center of the forceps rings. At block 208, a guide wire is inserted through the needle (0.93 mm O.D).

Figure 16:
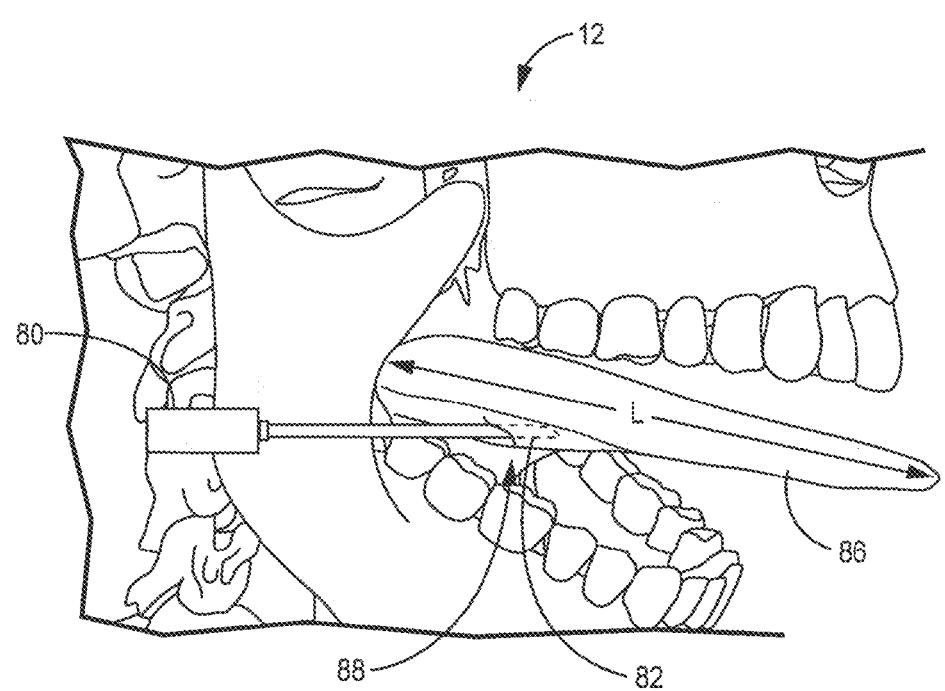
FIG. 16 is a schematic diagram of a side view of a distal end of the needle piercing the base of the tongue depicted in FIG. 15.
Figure 17:
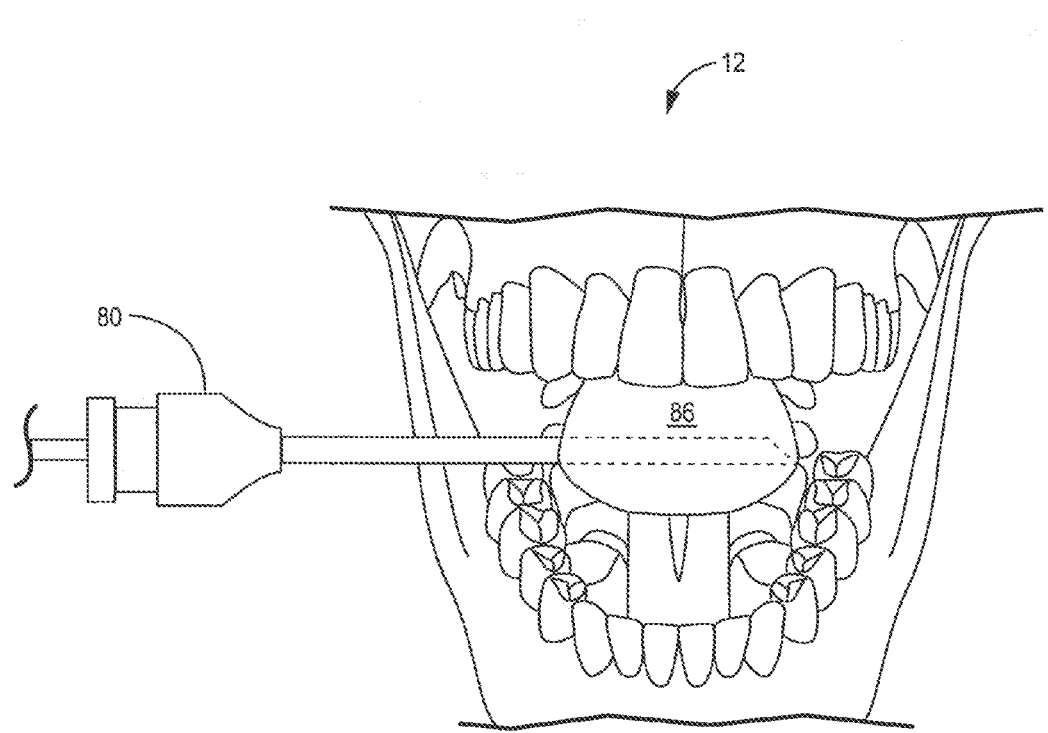
FIG. 17 is a schematic diagram of a front view of a distal end of the needle piercing the base of the tongue depicted in FIG. 16.

At block 210, the needle is removed. Referring to FIGS. 16-17, a needle 80 approaches one side of the tongue 80. At block 212, the trocar (12 French (Fr), 4 mm outer diameter) is inserted with a cannula (~4.7 mm O.D.) over the guide wire. At block 214, the guide wire and trocar are removed. At block 216, a lead 42 is selected that will fit the tongue. The lead 42 can have a length of about 4-6 mm less than the width of the tongue where the cannula is positioned. The forceps are gently released. The width of the tongue can be marked on the cannula for the appropriate size lead marking system.

Figure 18:
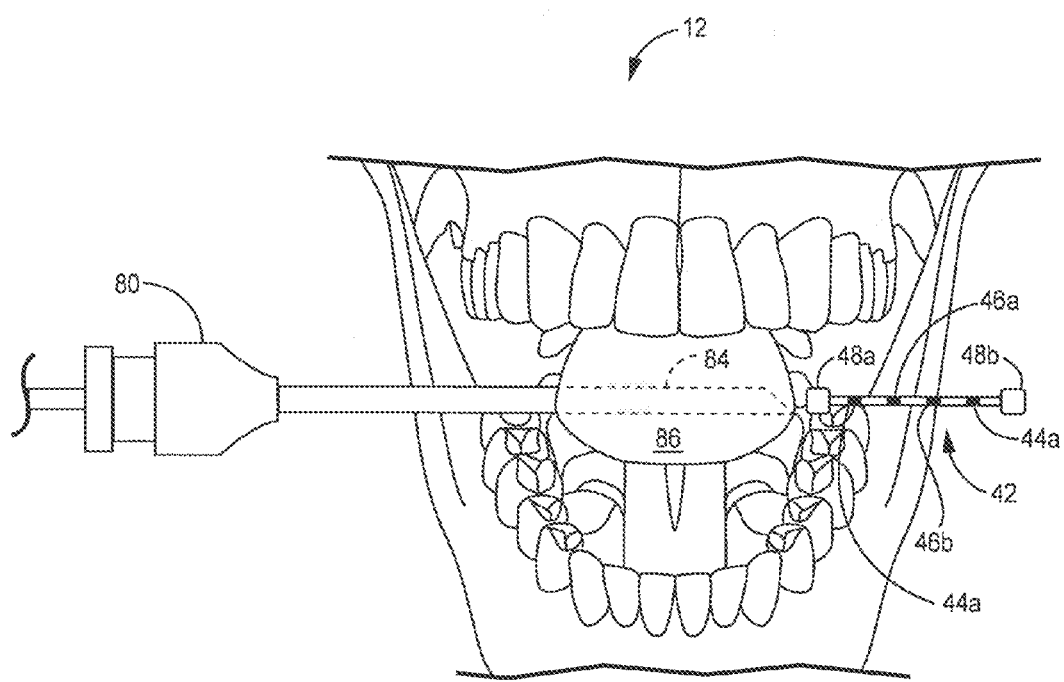
FIG. 18 is a schematic diagram of a front view of a distal end of the needle piercing a side of the base of the tongue while a lead is positioned near a lumen of the needle on the opposing side of the base of the tongue.
Figure 23:
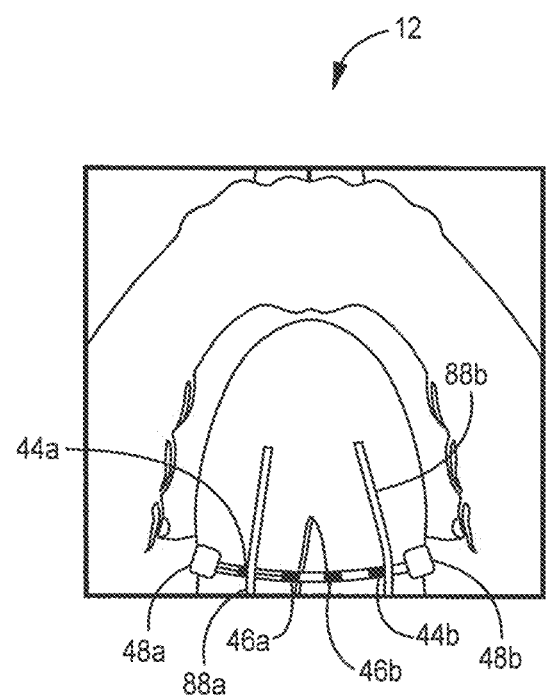
FIG. 23 is a schematic diagram of a bottom view of a lead implanted into the base of the tongue.

The needle pierces the base 87 of the tongue, in order to begin the process of creating an elongated aperture in the tongue 86 that is perpendicular to the length L or longitudinal axis of the tongue 86. The puncture is typically created in the base of the tongue; however, other locations may also be suitable and may be patient specific. The needle 80 is moved in a medial-lateral or sideways direction, as shown by FIG. 16-17. After fully creating the aperture through the base 87 of the tongue, the first end 45a of the lead 42 is positioned near the lumen 84 of the needle 80, as shown in FIG. 18. The lead 42 is continuously moved through the lumen 84 until the lead 42 is fully or almost fully inserted into the lumen 84 of the needle 80, as shown in FIG. 19-20. The needle 80 is gradually removed by pulling the needle 80 in a reverse or proximal direction. As the needle 80 is removed, the lead 42 is slowly moved further into the tongue, as shown in FIG. 20. The needle 80 is then fully removed from the base 87 of the tongue, as shown in FIG. 21. The first and second electrodes are positioned over a first and second hypoglossal nerve 88a,b, as is shown in FIG. 23. Since the base of the tongue does not substantially move, the electrodes 44a,b, 46a,b substantially stay in position relative to the first and second hypoglossal nerves 88a,b. In particular, the electrodes 44a,b, 46a,b remain in close proximity of the hypoglossal nerves to continue to effectively and efficiently stimulation the nerves in order to move the tongue. A mounting retainer 16, that includes an electrical stimulator 30 connected to contact electrodes or transmitting interface as shown in FIG. 1. The mounting retainer 16 is configured to snuggly fit over a patient's lower set of teeth and to snap into position.

Figure 30:
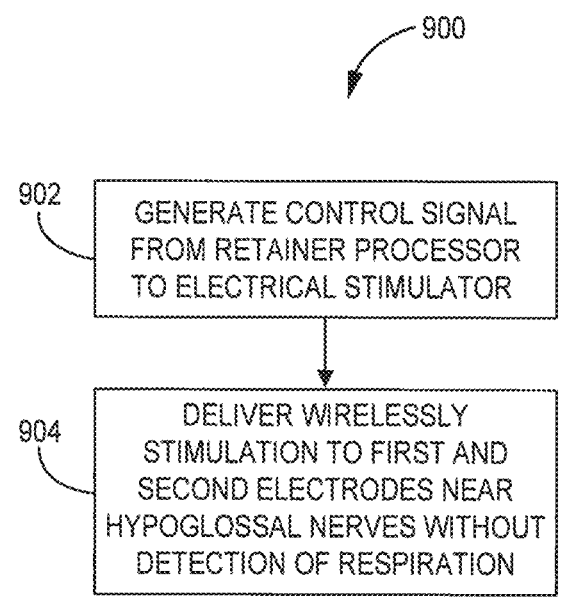
FIG. 30 is a flow diagram for using a dental system to reduce or eliminate the effects of obstructive sleep apnea.

FIG. 30 is a flow diagram for a method 900 to use a neural stimulation device to effectively stimulate the first and second hypoglossal nerves in order to reduce or eliminate the effects of obstructive sleep apnea. Method 900 employs a removable oral device comprising an electrical stimulator and a single lead with a first and a second electrode are employed. The electrical stimulator is mounted on a polymeric portion 16 configured to align with outer surfaces of a set of teeth. Method 900, comprises generating a control signal from a processor associated with one or more electrical stimulators 30 to a pulse generator at block 902. In response to the control signal from the processor, electrical signal(s) are repeatedly generated by the pulse generator and wirelessly transmitted from the transmitting antenna(s) 32a,b to the receiving antenna(s) 48a,b. The electrical signal(s) is conducted from the receiving antenna to the receiving antenna and electrodes on lead 42 and thereby paces the neural (and/or muscular) tissue site(s). The pacing vector is formed using electrodes comprising an anode and a cathode. The pacing vector paces neural tissue proximate or near a first and a second hypoglossal nerve. The lead lacks a mechanical connection to the polymeric portion. Optionally, a timer is employed in order to deliver electrical stimulation to the first and second electrodes after a first delay determined by a timer. The timer delays delivery of electrical stimulation until a patient is asleep. Generation of the electrical stimulation to the first and second electrodes occurs without using a sensor for detecting respiration by a patient at block 904.

Electrodes are spaced apart along the lead in order to stimulate a left and right hypoglossal nerves. The stimulation of the neural tissue can be set through a programmer by the user or physician. Alternatively, dental system 10 can automatically set stimulation parameters using historical data. The electrical field (e.g. amplitude, pulse width duration, etc.) must be set sufficiently high such that the muscle tone keeps the tongue from moving to the back of the mouth to avoid blocking the upper airway or moves the tongue forward to open the upper airway if blocked. Additionally, the processor is configured to track the history of settings (e.g. amplitude, pulse duration etc.) that effectively capture the tissue. By varying the electrical field, and/or duty cycle between the left and right hypoglossal nerve-nerve fatigue is avoided.

The stimulation system of the present disclosure is a substantial improvement over conventional OSA devices. For example, some conventional devices employ a single cuff electrode attached to the hypoglossal nerve. To avoid fatigue of nerve, some conventional systems detect inspiration with a pressure sensor placed in a patient's chest which is a relatively complex system. One or more embodiments of the present disclosure does not detect inspiration or expiration thereby allowing the dental system to more easily manufactured and operated and requires less surgery for implantation. Additionally, the presently disclosed device can easily have its battery replaced. Moreover, if the patient does not like the device, the lead can be easily removed. To remove the lead, a small incision on one side of the tongue is made to expose the lead. The lead would then be pulled out from that side.

The present disclosure stimulates both hypoglossal nerves with one lead but varies the electrical field so that fatigue of the nerves can be avoided. For example, a switching cycle may be implemented 5 seconds to 1 minute. The stimulator remains on continuously when the patient begins to sleep and until the patient wakes. In one or more embodiments, a patient may turn on a timer for the stimulator to remain continuously on to deliver electrical stimulation pulses. Optionally, a timer could be included in the electrical stimulator 30, as shown in FIG. 12. The present stimulation keeps tone in the muscles sufficiently high enough to ensure the tongue cannot move to block the back of the throat and does not close so that gagging can occur while the patient is sleeping.

One or more embodiments can detect breathing to determine when to turn on or turn of electrical stimulation.

The device and technique described herein can be cheaply produced and implemented with reduced risk to the patient compared to conventional devices. The techniques and apparatus described in this disclosure allow an oral device to repeatedly stimulate the hypoglossal nerves to move the tongue in order to avoid or eliminate the effects of obstructive sleep apnea (OSA). Delivery of electrical stimulation to the hypoglossal nerves occurs without detection of respiration, which is required by some conventional devices.

It should be appreciated that the dental system 10 can be configured to have a variety of different dimensions. Exemplary dimensions of a dental system 10 are generally shown in FIG. 2 and provided below. The length D1 of the lead body 43 is about 23 mm and the lead body thickness is 1.27 mm. Receiver 48a is about 4.5 mm whereas receiver 48b is about 5 mm. Electrode 24 width is about 1.5 mm. Midline separation between electrode 46a,b and the midline of the tongue is about 4 mm. Electrode separation between electrodes 46a,b and 24 are 1.5 mm. Lead 42 may comprise a Medtronic deep brain stimulation quadripolar lead such as a lead that is similar to deep brain stimulation leads (DBS) (e.g. DBS lead 3387, DBS lead 3389, DBS lead 3391, all of which are commercially available from Medtronic, Inc.)

Figure 5:
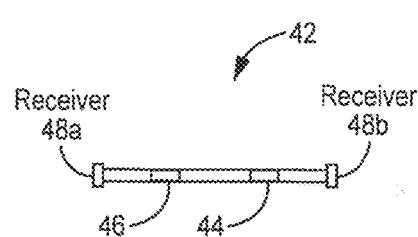
FIG. 5 is a schematic diagram of an example medical electrical lead that includes a set of bipolar electrodes and receivers (e.g. inductive receivers) that can be employed in the system shown in FIG. 1.
Figure 6:
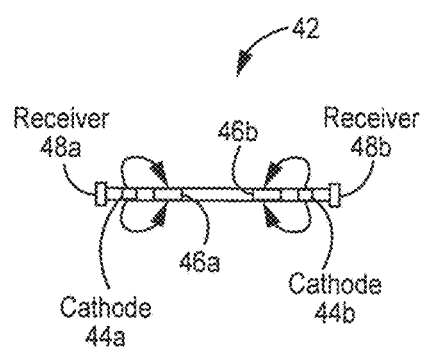
FIG. 6 is a schematic diagram of a medical electrical lead that includes a set of quadrapolar electrodes and energy receivers that can be employed in the system shown in FIG. 1.

Exemplary measurements for lead 42 can include 3 millimeters (mm) electrodes with 4 mm spacing, 2.5 cm wide end to end, and 1.27 mm diameter as shown, for example, in FIGS. 5-6. FIG. 2 also shows that the distance D5 between a first and second antenna 32a,b is about 30 mm. D3 (FIG. 1) was measured second and third molar on dental device 14. The distance D6 (FIG. 2) between the antenna 32a and the receiver 48a is about 3.5 mm. The mounting retainer flange 34 has a thickness of about 1 mm. The antenna 32b and encapsulation or shrink wrapped polymeric thickness can be up to about 2 mm. The shrink wrapped polymeric thickness can be up to about 0.5 mm.

The following paragraphs enumerated consecutively from 1-37 provide for various aspects of the present disclosure. In one embodiment, in a first paragraph (1) the present disclosure provides a first embodiment dental system for treating obstructive sleep apnea, the system comprising:

a removable mounting retainer configured to align with a set of teeth;

an electrical stimulator coupled to the mounting retainer; and a lead comprising a lead body and one or more electrodes along the lead body, the one or more electrodes positioned to stimulate hypoglossal neural tissue to cause a tongue to move in response to the electrical stimulator wirelessly delivering electrical signals to the one or more electrodes.

Embodiment 2 is a system of embodiment 1 wherein delivering electrical signals occurs without monitoring any phase of respiration.

Embodiment 3 is a system of any of embodiments 1-2 wherein the lead having a longitudinal axis extending from a first and a second end, the one or more electrodes comprising first and second electrodes at the first and second ends, respectively the first electrode positioned proximate a first hypoglossal nerve and the second electrode positioned proximate a second hypoglossal nerve.

Embodiment 4 is a system of any of embodiments 1-3 wherein the lead being curvilinear extending from a first and a second end, the one or more electrodes comprising first and second electrodes at the first and second ends, respectively the first electrode positioned proximate a first hypoglossal nerve and the second electrode positioned proximate a second hypoglossal nerve.

Embodiment 5 is a system of any of embodiments 1-4 wherein the neural tissue comprises at least one of first or second hypoglossal nerves.

Embodiment 6 is a system of any of embodiments 1-5 wherein the lead lacks a mechanical connection to the mounting retainer.

Embodiment 7 is a system of any of embodiments 1-6 further comprising:

a transmitting antenna coupled to the electrical stimulator;

first and second receiving antennas coupled to the first and second ends of the lead, respectively, the first and the second electrodes coupled to the first and the second receiving antennas, respectively.

Embodiment 8 is a system of any of embodiments 1-7 wherein the transmitting antenna is electrically coupled to the first and a second receiving antennas on the lead while delivering electrical signals from the electrical stimulator to one of the first and second electrodes.

Embodiment 9 is a system of any of embodiments 1-8 wherein the lead is disposed perpendicular to a longitudinal axis of a patient's tongue such that the first electrode is less than 2 millimeter (mm) from the first hypoglossal nerve and the second electrode is less than 2 mm from the second hypoglossal nerve.

Embodiment 10 is a system of any of embodiments 1-9 wherein a transmitting antenna is configured to transmit electrical signals from the electrical stimulator to the first and second receiving antennas, the transmitting antenna mechanically coupled to the mounting retainer.

Embodiment 11 is a system of any of embodiments 1-10 wherein the first and second receiving antennas comprising conductive wire wounded about itself, wherein the transmitting antenna having conductive wire wound in a substantially rectangular shape.

Embodiment 12 is a system of any of embodiments 1-11 wherein the first and second receiving antennas comprising conductive wire wounded about itself over a non-conductive material, wherein the transmitting antenna having the conductive wire wound about itself in a substantially rectangular shape.

Embodiment 13 is a device of any of embodiments 1-12 wherein the first and second receiving antennas comprising conductive wire wounded about itself over a non-conductive material, wherein the transmitting antenna having the conductive wire wound about itself in a substantially circular shape.

Embodiment 14 is a device of any of embodiments 1-13 wherein the electrical stimulator comprises:

a processor, a pulse generator coupled to the processor, and a power source coupled to the processor and to the pulse generator, the processor signals the pulse generator to generate an electrical signal from the power source to the transmitting antenna, the transmitting antenna wirelessly transmits the electrical signals to the first and second receiving antennas, which then conducts to the first and second electrodes.

Embodiment 15 is a device of any of embodiments 1-16 further comprising:

a timer, coupled to the processor, for timing delivery of electrical stimulation to one of the first and second electrodes.

Embodiment 16 is a device of any of embodiments 1-17 a microphone, coupled to the processor, configured to acquire sounds from a person.

Embodiment 17 is a device of any of embodiments 1-18 wherein the timer times delivery of electrical stimulation after the patient is asleep.

Embodiment 18 is a device of any of embodiments 1-17 wherein the processor is further configured to compare sound from the patient to sleeping sounds stored in memory.

Embodiment 19 is a device of any of embodiments 1-18 wherein the microphone acquires sleeping sounds from the person over time, the sleeping sounds are stored into memory;

the processor is configured to distinguish sleeping sounds from non-sleeping sounds using sleeping sounds acquired over time and a template matching technique.

Embodiment 20 is a device of any of embodiments 1-19 wherein the processor is configured to track time duration that sleeping sounds progressively increases in intensity over time.

Embodiment 21 is a device of any of embodiments 1-19 wherein the processor automatically generates a control signal to a pulse generator to generate electrical stimulation in response to the processor determining that the microphone has acquired sleeping sounds.

Embodiment 22 is a device of any of embodiments 1-21 wherein the processor automatically signals the pulse generator to suspend delivering electrical stimulation in response to the processor determining that the microphone has acquired non-sleeping sounds from the patient.

Embodiment 23 is a device of any of embodiments 1-22 wherein delivering the electrical signals to one of the first and second electrodes occurs without using a sensor for detecting breathing by a patient.

Embodiment 24 is a device of any of embodiments 1-23 wherein electrical stimulation is adjusted from the pulse generator to one of the first and second electrodes to ensure tone is sufficiently high to keep the upper airway open.

Embodiment 25 is a device of any of embodiments 1-24 wherein as the processor generates a control signal for device output in response to detection of a sleeping sound(s).
Embodiment 26 is a device of any of embodiments 1-26 wherein a timer can be used to turn on the pulse generator after a certain time period through one of a timer or other condition.
Embodiment 27 is a device of any of embodiments 27-wherein the time period can be set in thirty minutes or less.
Embodiment 27a is a device of any of embodiments 1-27 wherein the first and second electrodes are not cuff electrodes.
Embodiment 28 is a device of any of embodiments 1-27a wherein the first and second electrodes simultaneously or about simultaneously deliver electrical stimulation to surrounding tissue.
Embodiment 29 is a device of any of embodiments 1-28 wherein the lead is a quadripolar lead.
Embodiment 30 is a device of any of embodiments 1-29 wherein the lead comprises two electrodes to stimulate first hypoglossal neural tissue and two other electrodes to stimulate a second hypoglossal neural tissue.
Embodiment 31 is a device of any of embodiments 1-30 wherein the quadripolar lead includes substantially equally spaced apart electrodes.
Embodiment 32 is a device of any of embodiments 1-31 wherein the quadripolar lead includes closely spaced apart electrodes.
Embodiment 33 is a device of any of embodiments 1-32 wherein the battery is rechargeable.
Embodiment 34 is a device of any of embodiments 1-33 wherein inspiration is not detected to a time of delivery of the stimulation pulses.
Embodiment 35 is a device of any of embodiments 1-34 wherein expiration is not detected to time a delivery of the stimulation pulses.
Embodiment 36 is a device of any of embodiments 1-35 wherein the electrodes are placed in or near other muscles or nerves of the upper airway to prevent upper airway closure.
Embodiment 37 is a method of any of embodiments 1-36 with a processor, controlling a stimulation generator to alternately and wirelessly deliver electrical stimulation to first and second tissue sites proximate to first and second hypoglossal nerves, respectively of a patient to cause at least a portion of a tongue to move.
Embodiment 38 is a method of any of embodiments 1-wherein delivering electrical signals occurs without monitoring any phase of respiration.
Embodiment 39 is a method of any of embodiments 37 wherein the stimulation generator is coupled to the mounting retainer.
Embodiment 40 is a method of any of embodiments 37-39 wherein a lead having a first and second pacing electrode is not mechanically coupled to the mounting retainer.
Embodiment 41 is a method of any of embodiments 37-40 further comprising:
coupling a timer to the processor; and
using a timer to time delivery of electrical stimulation to the first and second tissue sites.
Embodiment 41 is a method of any of embodiments 37-40 wherein the timer delays delivery of electrical stimulation until a patient is asleep.
44. The device of claim 38 further comprising detecting a sleep state by monitoring one of breathing sounds, tongue movement, and tongue muscle.
45. The method of claim 38 wherein generation of the electrical stimulation to the first and second electrodes occurs without using a sensor for detecting respiration by a patient.
46. The method of claim 38 wherein generation of the electrical stimulation to the first and second electrodes occurs without using a sensor for detecting inspiration by a patient.
47. The method of claim 38 wherein electrical stimulation is adjusted to ensure tone is sufficiently high to cause movement of the tongue.
48. The method of claim 42 wherein the timer is used to turn on the pulse generator after a delay.
49. The method of claim 48 wherein the delay is based upon one of a condition and a preset time.
50. The method of claim 49 wherein the time period can be set in thirty minutes or less.
51. The method of claim 49 wherein the time period can be set based upon time increments using historical data acquired from the patient.
52. The method of claim 38 wherein the first and second electrodes are not cuff electrodes.
53. The method of claim 38 wherein the first and second electrodes substantially simultaneously deliver electrical stimulation to surrounding tissue.
54. The method of claim 38 wherein the lead is a quadripolar lead.
55. The method of claim 54 wherein the quadripolar lead includes substantially equally spaced apart electrodes.
56. A oral device for moving a tongue comprising:
a mounting retainer configured to align with a set of teeth;
an electrical stimulator coupled to the mounting retainer;
a first antenna coupled to the electrical stimulator;
a lead having a longitudinal axis extending from a first to a second end, a second antenna coupled to the lead, the lead lacking a mechanical connection to the mounting retainer; and
a first electrode coupled to the second antenna.
57. A pacing device means, comprising means, responsive to received trigger signals from a pericutaneously implanted lead, for delivering pacing pulses to the neural tissue,
wherein the lead is not mechanically connected to the pacing device.
58. A system comprising:
means for generating and delivering energy through a lead not mechanically connected to the stimulation generator; and
means for controlling the means for generating and delivering energy to deliver electrical stimulation to one or more tissue sites proximate to one or hypoglossal nerves, wherein the lead is not mechanically connected to the stimulation generator.
59. The system of claim 28 wherein means for delivering energy occurs without monitoring any phase of respiration.
60. A computer-readable medium comprising instructions that, when executed by a processor, cause the processor to control a stimulation generator to deliver electrical stimulation to one or more tissue sites proximate to one or more of hypoglossal nerves with a processor, controlling a stimulation generator to alternately and wirelessly deliver electrical stimulation to first and second tissue sites proximate to first and second hypoglossal nerves, respectively of a patient to cause at least a portion of a tongue to move.
61. The medium of claim 60 wherein delivering electrical signals occurs without monitoring any phase of respiration.
62. A method of making a dental system for treating obstructive sleep apnea comprising:

providing a mounting retainer;
coupling an electrical stimulator to the mounting retainer;
coupling an antenna to the mounting retainer, the antenna configured to wirelessly transmit energy to a lead that is not mechanically connected to the mounting retainer.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

The invention claimed is:

1. A dental system for treating obstructive sleep apnea, the system comprising:
   a removable mounting retainer configured to align with a set of teeth;
   an electrical stimulator coupled to the mounting retainer;
   a lead comprising a lead body and one or more electrodes along the lead body, the one or more electrodes positioned to stimulate hypoglossal neural tissue to cause a tongue to move in response to the electrical stimulator wirelessly delivering electrical signals to the one or more electrodes
   a transmitting antenna coupled to the electrical stimulator;
   first and second receiving antennas coupled to first and second ends of the lead, respectively, the first and the second electrodes coupled to the first and the second receiving antennas, respectively.

2. The device of claim 1 wherein delivering electrical signals occurs without monitoring any phase of respiration.

3. The device of claim 1 wherein the lead has a longitudinal axis extending from the first to the second end, the one or more electrodes comprising first and second electrodes at the first and second ends, respectively the first electrode positioned proximate a first hypoglossal nerve and the second electrode positioned proximate a second hypoglossal nerve.

4. The device of claim 3 wherein the first and second receiving antennas comprise conductive wire wounded about itself and wherein the transmitting antenna comprises conductive wire wound in a substantially rectangular shape.

5. The device of claim 3 wherein the first and second receiving antennas comprise conductive wire wounded about itself over a non-conductive material and wherein the transmitting antenna comprises conductive wire wound about itself in a substantially rectangular shape.

6. The device of claim 3 wherein the first and second receiving antennas comprise conductive wire wounded about itself over a non-conductive material and wherein the transmitting antenna comprises conductive wire wound about itself in a substantially circular shape.

7. The device of claim 1 wherein the lead is curvilinear extending from the first to the second end, the one or more electrodes comprising first and second electrodes at the first and second ends, respectively the first electrode positioned proximate a first hypoglossal nerve and the second electrode positioned proximate a second hypoglossal nerve.

8. The device of claim 1 wherein the neural tissue comprises at least one of first or second hypoglossal nerves.

9. The device of claim 1 wherein the lead lacks a mechanical connection to the mounting retainer.

10. The device of claim 9 wherein a timer can be used to turn on the electrical stimulator after a certain time period through one of a timer or other condition.

11. The device of claim 10 wherein the time period can be set in thirty minutes or less.

12. The device of claim 1 wherein the transmitting antenna is electrically coupled to the first and a second receiving antennas on the lead while delivering electrical signals from the electrical stimulator to one of the first and second electrodes.

13. The device of claim 1 wherein the lead is disposed perpendicular to a longitudinal axis of a patient's tongue such that the first electrode is less than 2 millimeter (mm) from the first hypoglossal nerve and the second electrode is less than 2 mm from the second hypoglossal nerve.

14. The device of claim 1 wherein a transmitting antenna is configured to transmit electrical signals from the electrical stimulator to the first and second receiving antennas, the transmitting antenna mechanically coupled to the mounting retainer.

15. The device of claim 1 wherein the electrical stimulator comprises:
   a processor, a pulse generator coupled to the processor, and a power source coupled to the processor and to the pulse generator, wherein the processor signals the pulse generator to generate an electrical signal from the power source to the transmitting antenna and the transmitting antenna wirelessly transmits the electrical signals to the first and second receiving antennas, which then conducts to the first and second electrodes.

16. The device of claim 15 further comprising:
   a timer, coupled to the processor, for timing delivery of electrical stimulation to one of the first and second electrodes.

17. The device of claim 16 wherein the timer times delivery of electrical stimulation after the patient is asleep.

18. The device of claim 15 further comprising:
   a microphone, coupled to the processor, configured to acquire sounds from a person.

19. The device of claim 18 wherein as the processor generates a control signal for device output in response to detection of a sleeping sound(s).

20. The device of claim 18 wherein the processor is further configured to compare sound from the patient to sleeping sounds stored in memory.

21. The device of claim 18 wherein the microphone acquires sleeping sounds from the person over time, the sleeping sounds are stored into memory; and
   wherein the processor is configured to distinguish sleeping sounds from non-sleeping sounds using sleeping sounds acquired over time and a template matching technique.

22. The device of claim 21 wherein the processor is configured to track time duration that sleeping sounds progressively increases in intensity over time.

23. The device of claim 18 wherein the processor automatically generates a control signal to the electrical stimulator to generate electrical stimulation in response to the processor determining that the microphone has acquired sleeping sounds.

24. The device of claim 18 wherein the processor automatically signals the electrical stimulator to suspend delivering electrical stimulation in response to the processor determining that the microphone has acquired non-sleeping sounds from the patient.

25. The device of claim 1 wherein delivering the electrical signals to one of the first and second electrodes occurs without using a sensor for detecting breathing by a patient.

26. The device of claim 25 wherein electrical stimulation is adjusted from the electrical stimulator to one of the first and second electrodes to ensure tone is sufficiently high to keep the upper airway open.

27. The device of claim 1 wherein the first and second electrodes are not cuff electrodes.

28. The device of claim 1 wherein the first and second electrodes simultaneously or about simultaneously deliver electrical stimulation to surrounding tissue.

29. The device of claim 1 further comprising a battery and wherein the battery is rechargeable.

30. The device of claim 1 wherein inspiration is not detected to a time of delivery of the stimulation pulses.

31. The device of claim 1 wherein expiration is not detected to time a delivery of the stimulation pulses.

32. The device of claim 1 wherein the electrodes are placed in or near other muscles or nerves of the upper airway to prevent upper airway closure.

33. A dental system for treating obstructive sleep apnea, the system comprising:
   a removable mounting retainer configured to align with a set of teeth;
   an electrical stimulator coupled to the mounting retainer;
   a lead comprising a lead body and one or more electrodes along the lead body, the one or more electrodes positioned to stimulate hypoglossal neural tissue to cause a tongue to move in response to the electrical stimulator wirelessly delivering electrical signals to the one or more electrodes, wherein the lead is a quadripolar lead.

34. The device of claim 33 wherein the lead comprises two electrodes to stimulate first hypoglossal neural tissue and two other electrodes to stimulate a second hypoglossal neural tissue.

35. The device of claim 33 wherein the quadripolar lead includes substantially equally spaced apart electrodes.

36. The device of claim 33 wherein the quadripolar lead includes closely spaced apart electrodes.

37. The device of claim 36 wherein the closely spaced apart electrodes are spaced apart by less than 1.5 milimeters.

* * * * *